United States Patent [19]

Ferraris et al.

[11] Patent Number: 5,274,058
[45] Date of Patent: Dec. 28, 1993

[54] LOW BANDGAP POLYMERS RF FUSED BITHIOPHENES

[75] Inventors: John P. Ferraris, Dallas; Tim L. Lambert, Austin; Santiago Rodriguez, Richardson, all of Tex.

[73] Assignee: Board of Regents, The University of Texas System, Austin, Tex.

[21] Appl. No.: 758,859

[22] Filed: Sep. 12, 1991

[51] Int. Cl.$^5$ ............................................. C08G 75/00
[52] U.S. Cl. ..................................... 526/256; 252/500; 528/360; 528/377; 528/380
[58] Field of Search ................ 526/256; 528/360, 377, 528/380

[56] References Cited

U.S. PATENT DOCUMENTS 3,987,060 10/1976 Hashimoto .......................... 260/329

OTHER PUBLICATIONS

Amer et al., (1989), *Phosphorous Sulfur and Silicon*, 42:63-71.
Bakhshi et al., (1988), *Solid State Comm.*, 65:1203-1206.
Bolognesi et al., (1988), *J. C. S. Chem. Comm.*, 246-247.
Bredas, J. L., (1985), *J. Chem. Phys.*, 82:3808-3811.
Bredas, J. L., (1987), *Synthetic Metals*, 17:115-121.
Bredas et al., (1986), *J. Chem. Phys.*, 85:4673-4678.
Bredas et al., (1982), *Phys. Rev.*, B26:5843-5854.
Bredas et al., (1984), *Synthetic Metals*, 9:265-275.
Charles, G., (1963), *Bull. Soc. Chim. Fr.*, 1573-1576.
Chung et al., (1984), *Phys. Rev. B*, 30:702-710.
Colaneri et al., (1986), *Synthetic Metals*, 14:45-52.
Ferraris et al., (1990), *New Polym. Mater.*, 2:41-65.
Ferraris et al., (1989), *J. C. S. Chem. Comm.*, 1318-1320.
Ferraris et al., (1991), *Polym. Mater. Sci. Engn.*, 64:332-333.
Charles, G., (1960), *Bull. Soc. Chim. Fr.*, 421.
Grant et al., (1979), *Solid State Commun.*, 29(3):225-229.
Hanack et al., (1991), *Polym. Mater. Sci. Engn.*, 64:330-331.
Havinga et al., (1989), *Chem. Mater.*, 1:650-659.
Ikenoue et al., (1991), *Synthetic Metals*, 40:1-12.
Ikenoue, Y., (1990), *Synthetic Metals*, 35:263-270.
Jenekhe, S. A., (1986), *Nature*, 322:345-347.
Jones et al., (1990), *J. Phys. Chem.*, 94:5761-5766.
Jordens et al., (1970), *J. Chem. Soc.*, (C):273-277.
Jow et al., (1986), *Synthetic Metals*, 14:53-60.
Kaufman et al., (1983), *Solid State Comm.*, 47(8):585-589.
Kertesz et al., (1989), *Synthetic Metals*, 28:C545-552.
Kertesz et al., (1987), *J. Chem. Phys.*, 91:2690-2692.
Kobayashi et al., (1985), *J. Chem. Phys.*, 82(12):5717-5723.
Koster et al., (1974), *J. C. S. Perkin II*, 803-806.

(List continued on next page.)

Primary Examiner—Christopher Henderson
Attorney, Agent, or Firm—Arnold, White & Durkee

[57] ABSTRACT

The present invention involves monomeric compounds having the structure:

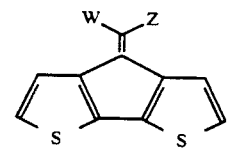

Substituents W and Z are independently —CN, —NO$_2$, -aryl, -aryl-V, —COX, SO$_2$R, —H, or -alkyl. Substituent X is —OR, or —NR,R where R and R$^1$ are independently -alkyl or —H. Substituent V is -halide, —NO$_2$, —CN, —SO$_2$R, or —COX. At least one of W and Z is —NO$_2$, —SO$_2$R, —CN, —COX or -aryl-V. In one preferred embodiment substituents W and Z are both —CN. In another preferred embodiment, substituent X is —NO$_2$ or —CN and substituent Z is —C$_6$H$_4$NO$_2$. These monomers are polymerized to form low bandgap polymers.

5 Claims, 15 Drawing Sheets

OTHER PUBLICATIONS

*Chemical Abstracts*, vol. 115, Abstract No. 50431e, published in USA.

Koβmehl, Gerhard, (1979), "Semiconductive Conjugated Polymers", *Ber. Bunsenges. Phys. Chem.*, 83:417–426, published in Europe.

Amer et al., (1989), "Studies of Some Hindered 2,2'-Bithienyls and 3,3'-Bridged 2,2'-Bithienyls with Special Reference to Their UV Spectra and Oxidation Potentials", *Phosphorus, Sulfur, and Silicon*, 42:63–71, published in Europe.

Koster et al., (1976), *J. Chem. Soc., Perkin II*, 323–328.

Koster et al., (1979), *J. Chem. Soc., Perkin II*, 393–397.

Kowalik et al., (1991), *Poly. Mater. Engn. Sci.*, 64:214–215.

Lambert et al., (1991), *J. Chem. Soc. Chem. Commun.*, 752–754.

Lee et al., (1990), *Chem. Mater.*, 2:526–530.

Lee et al., (1988), *J. Chem. Phys.*, 88:2609–2617.

Lowe et al., (1984), *J. Am. Chem. Soc.*, 106:5837–5841.

Mintmire et al., (1987), *Synthetic Metals*, 16:235–243.

Otto et al., (1990), *Synth. Met.*, 36:327–335.

Patil et al., (1987), *Synth. Met.*, 20:151–158.

Patil et al., (1988), *Macromolecules*, 21:540–542.

Roncali et al., (1987), *J. Phys. Chem.*, 91:6706–6714.

Taliani et al., (1989), *Synthetic Metals*, 28:C507–C514.

Tanaka et al, (1988), *Synthetic Metals*, 24:371–377.

Tanaka et al., (1989), *Synthetic Metals*, 30:57–65.

Tanaka et al., (1985), *Phys. Rev. B*, 32(6):4279–4281.

Tanaka et al., (1987), *Synthetic Metals*, 20:333–345.

Toussaint et al., (1989), *J. Chem. Phys.*, 91(3):1783–1788.

Toussaint et al., (1989), *Synthetic Metals*, 28:C205–C210.

Wudl et al., (1984), *J. Org. Chem.*, 49:3382–3384.

Wudl et al., (1988), *Nonlinear Optical and Electroactive Polymers*. Prasad, P. N. and Ulrich, D., eds.; Plenum Press: New York, pp. 393–400.

Yamamoto et al., (1981), *Chem. Lett.*, 1079–1082.

Zhou et al., (1989), *J. Amer. Chem. Soc.*, 111:7371–7379.

Koster et al., (1976), "Proton Nuclear Magnetic Resonance Studies of Protonated Cyclopentadithiophenones and Cyclopentadith=Iophens", *Chemical Abstracts*, 84:497, Abstract No. 104633j, published in USA.

Lambert et al., (1991), "Narrow Band Gap Polymers: Poly(cyclopenta[2,1-=b;3,4-b']dithiophen-4-one)",

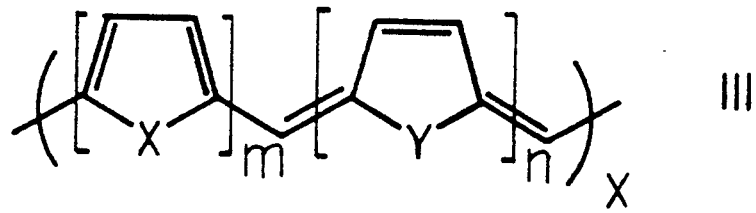
X, Y = S, NH, NR
*Fig. 3*
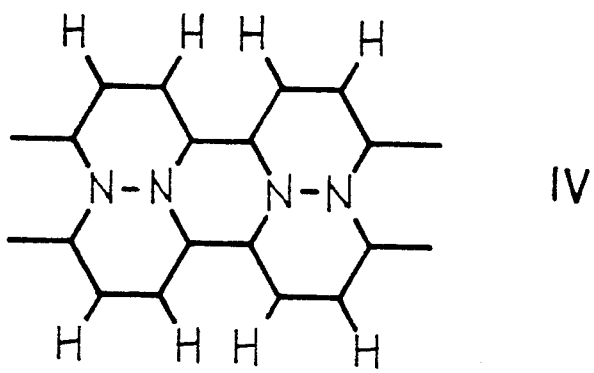
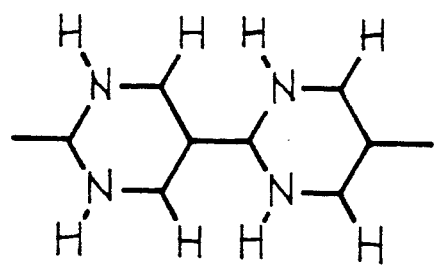
V
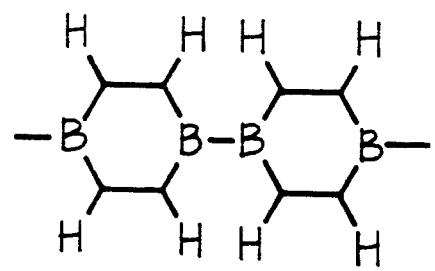
VI
*Fig. 4*

| X | HOMO(β) | $E^{mon}_{pa}$ (V vs SCE) | $E^{poly}_{pa}$ (V vs SCE) | HOMO-LUMO(β) | $E_{gap}$ (eV) |
|---|---|---|---|---|---|
| nil (bithiophene) | 0.32 | 1.2 | 0.7 | 1.02 | 2.0 (a) |
| S | 0.32 | 1.2 | 0.7 | 1.13 | 2.1 (b) |
| C=O | 0.32 | 1.2 | 0.8 | 0.46 | 1.2 (c) |
| C=C(CN)COOH | 0.32 | 1.2 | 0.7 | 0.34 | ≤0.9 |
| C=C(CN)COOEt | 0.32 | 1.2 | 0.8 | 0.34 | ≤0.9 |
| C=C(CN)$_2$ | 0.32 | 1.3 | 0.8 | 0.29 | 0.8 |
| C=C(CN)NO$_2$ | 0.32 | -- | -- | 0.03 | -- |

(a) SKOTHEIM (1986)
(b) JOW et al (1986)
(c) LAMBERT et al (1991)

SCHEME 1

IXa
CDT

IXb etc.

C2CCPD

CCPD

C16CCPD

C7CCPD

NPCCPD

LOW BANDGAP POLYMERS RF FUSED BITHIOPHENES

BACKGROUND OF THE INVENTION

Since the discovery of high electrical conductivity in "doped" polyacetylene films in the mid-1970's, the field of electroactive polymers has undergone explosive growth. The great interest in these materials stems from their potential use in electronic and optical applications. Electrical conductivity is typically achieved via oxidative (or, more rarely, reductive) doping of the neutral polymers, a practice which is often accompanied by reduced processibility and environmental stability. Hence a major goal in this field is the design and synthesis of processible polymers with low or zero bandgaps.

The potential benefits from such low gap polymers are well recognized and recent theoretical approaches have focused on bond length alternation (Bredas, et al., 1986; Toussaint, et al., 1989-2; Toussaint, et al., 1989-1; Bredas, J.L., 1985; Bakhashi, et al., 1987; Bredas, J.L., 1987; Kertesz, et al., 1987; Hanack, et al., 1991) and variations in occupancy of frontier orbitals (Tanaka, et al., 1985; Tanaka, et al., 1987; Tanaka, et al., 1989; Tanaka, et al., 1988) to identify likely low $E_{gap}$ systems. Polyisothianaphthene (PITN) (Wudl et al., 1984), I, and its derivatives (Ikenone et al., 1984), with $E_{gap} \approx 1.1$ eV represent some of the more successful experimental realizations of these theoretical predictions (Colaneri, et al., 1986; Kobayashi, et al., 1985). These polymers have $E_{gap}$'s 1 eV lower than their corresponding parent, polythiophene, (PT) (Bredas, J.L., 1985). This reduction in $E_{gap}$ is ascribed (Bredas et al., 1986) to an increased contribution of the quinoid structure, brought about by the 3,4-fused benzene ring. Thus, a considerable amount of the effort to date on narrow band gap polymers has concentrated on increasing their quinoid character. (See FIG. 1).

The energy difference between the aromatic and quinoid structure varies depending on the neutral material's degree of aromaticity. For polymers like polyphenylene, polythiophene, and polypyrrole, it can be substantial so that very little of the quinoid resonance form contributes to the neutral polymer's overall structure. Quinoid segments can be generated in these polymers by the doping process (Bredas, et al., 1984; Bredas, et al., 1982), however, and their growth followed by optical spectroscopy (Chung, et al., 1984). The energy dissimilarity is reduced in PITN since the creation of the quinoid structure in the thiophene moiety is partially compensated by return of aromaticity to the fused six membered ring. This observation has led to several other approaches for generating stable quinoid character. One (Toussaint, et al., 1989) is exemplified by structures like poly(2,7-pyrenylene vinylene), as shown in FIG. 2, structure IIa, to achieve the quinoid resonance form since in doing it exchanges one formally aromatic structure for another (bold outline).

Hence polymer IIa is predicted to have a significantly lower bandgap than the corresponding 1,6 isomer, IIb (see FIG. 2) which does not have this option (Toussaint, et al., 1989). A second approach does not rely on resonance stabilization to incorporate quinoid character but builds it directly into the monomer and polymer (Toussaint, et al., 1989; Bredas, J.L., 1987; Kertesz, et al., 1987; Hanack, et al., 1991; Jenekhe, S.A., 1986, Wudl, et al., 1988; Zimmer, et al., 1984; Yamamoto, et al., 1981; Miyaura, et al., 1981; Kobmehl, G., 1983). These materials are based on polyarene-methylidenes, III. Neutral films of III (X, Y = S, m=2, n=1) shown in FIG. 3 display absorption maxima around 900 nm (Hanack, et al., 1991), reminiscent of other lowered $E_{gap}$ polymers like PITN.

Yet another approach to lowered $E_{gap}$ materials exploits the band crossings between highest occupied (HO) and next highest occupied (NHO) orbitals or lowest unoccupied (LU) and next lowest unoccupied (NLU) orbitals (Tanaka, et al., 1987; Tanaka, et al., 1988) that occur in certain polymers like polyphenylene and polyperylene.

Theoretically, derivatives with lowered $E_{gap}$'s can be obtained by adjusting the frontier orbital occupancy of the polymer. This would be accomplished by replacing certain carbons with either electron rich (e.g., N) or electron poor (e.g., B) elements, their positions carefully chosen, while maintaining planarity. Systems predicted (Tanaka, et al., 1987; Tanaka, et al., 1988) to have lowered $E_{gap}$'s are structures IV, V and VI shown in FIG. 4. The synthesis of such materials, however, could be arduous and their processibility is not expected to be high.

When adding heteroatoms, substituents and ring fusions, the symmetry of the frontier orbitals must be considered. Unlike polyacetylene whose bandgap depends primarily on the average bond length alternation ($\delta r$), this effect is a secondary contributor to the $E_{gap}$ of polyheteroaromatics. This parameter is defined as the average of the difference of neighboring long and short C—C bonds. $E_{gap}$ is a minimum $\delta r = 0$. (Lowe, et al., 1984; Grant, et al., 1979; Longuet-Higgins, et al., 1959; Kertesz, et al., 1988; Paldus, et al., 1983). The dominant factor for heteroaromatics, however, is the strength of the interaction between the carbon framework and the heteroatom and this is dependent on the symmetry of the former's frontier orbitals (Lee, et al., 1988; Mintmire, et al., 1987). When the highest occupied molecular orbital (HOMO) is antisymmetric and the lowest unoccupied molecular orbital (LUMO) symmetric (as is the case for aromatic arrangements), the band gap increases upon interaction with the heteroatom. The bandgap is decreased, however, for the quinoidal bonding arrangement which has a symmetric HOMO and antisymmetric LUMO (see FIG. 5) (Lee, et al., 1988; Mintmire, et al., 1987). $E_{gap}$ is minimized at some intermediate structure. Thus polymers such as III, in which the frontier orbitals (HOMO and LUMO) are similarly perturbed by the heteroatom (thus canceling its effect) are expected to have reduced $E_{gap}$'s (Lee, et al., 1988; Kertesz, et al., 1989; Lee, et al., 1990).

Polymer VII, formed by annulating a second ring onto PITN, has been predicted by some to be a material with a vanishingly small $E_{gap}$ Subsequent calculations (Kertesz et al., 1989; Lee et al., 1990) and experimental measurements (Wudl, et al., 1990) showed that VII (shown in FIG. 6) had a bandgap greater than PITN.

SUMMARY OF THE INVENTION

The present invention involves monomeric compounds having the structure:

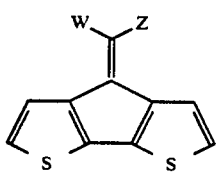

Substituents W and Z are independently —CN, —NO$_2$, -aryl, -aryl-V, —COX, SO$_2$R, —H, or -alkyl. Substituent X is —OR, or —NR,R where R and R$^1$ are independently -alkyl or -H. Substituent V is - halide, —NO$_2$, —CN, —SO$_2$R, or —COX. At least one of W and Z is —NO$_2$, —SO$_2$R, —CN, —COX or -aryl-V. In one preferred embodiment substituents W and Z are both —CN. In another preferred embodiment, substituent X is —NO$_2$ or —CN and substituent Z is - C$_6$H$_4$NO$_2$.

In a preferred embodiment, substituent W is —CN and substituent Z is —COX, —SO$_2$R, -alkyl, —H, aryl or -aryl-V. Substituent X is —OR or —NRR$^1$ where R and R$^1$ are independently —H or -alkyl. Substituent V is —NO$_2$, -halide, —CN or —SO$_2$R.

In another embodiment, substituent W is —CF$_3$ and substituent Z is —SO$_2$R where R is —H or -alkyl.

In another preferred aspect, substituent W is —NO$_2$ and substituent Z is H or CO$_2$R where R is —H or -alkyl.

A particularly preferred embodiment of the present invention involves a compound having the structure

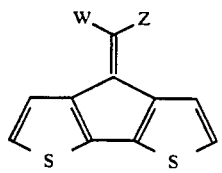

where substituent W is CN or NO$_2$ and substituent Z is CO$_2$R. Here, R is H or C$_m$H$_{2m+1}$ and m is 1 to about 16.

From a further View, the present invention concerns a compound having the structure

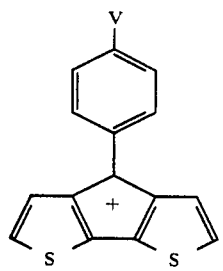

Substituent V is —NO$_2$, -halide, —OR$^1$ or —NR$^1$R$^2$. Substituents R$^1$ and R$^2$ are independently —H or -alkyl.

Another novel compound of the present invention is one having the structure:

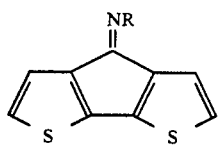

where R is H or alkyl. This compound, if aqueous or acidic conditions are avoided, may be polymerized into a low bandgap polymer.

In further view, the present invention includes novel low bandgap polymers. One such low bandgap polymer has the structure:

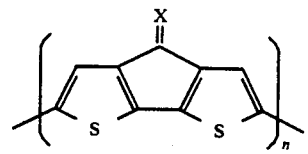

Substituent X is O or NR and R is —H or -alkyl. The number of monomeric units (n) is typically 5 to about 500.

Preferred low bandgap polymers of the present invention have the structure:

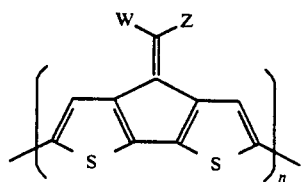

Substituents W and Z are independently —CN, —NO$_2$, -aryl, -aryl-V, —COX, —SO$_2$R, —H, or -alkyl. Substituent X is —OR or —NR,R$^1$, where R and R$^1$ are independently -alkyl or —H. Substituent V is -halide, —NO$_2$, —CN, —SO$_2$R, or —COX. At least one of substituents W and Z is —NO$_2$, —SO$_2$R, —CN, —COX or -aryl-V. The number of monomeric units (n) in the low bandgap polymer is 5 to about 500. In one preferred embodiment substituent W is —NO$_2$ and substituent Z is CO$_2$R where R is —H or -alkyl. In another preferred embodiment, substituent W is CN or NO$_2$ and substituent Z is CO$_2$R where R is H or C$_m$H$_{2m+1}$ and m is 1 to about 16. Additionally, where substituent W is CN or NO$_2$ and substituent Z is C$_6$H$_4$NO$_2$ an additional preferred polymer is described.

One preferred low bandgap polymer has the structure:

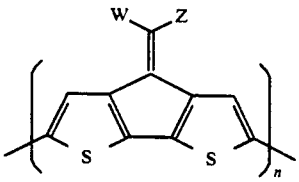

where substituent W is —CN and substituent Z is —COX, —SO$_2$R, -alkyl, —H, aryl or -aryl-V. Substituent X is —OR or —NRR$^1$ where R and R$^1$ are independently —H or alkyl. Substituent V is —NO$_2$, -halide, —CN or —SO$_2$R. The number of monomeric units (n) is again 5 to about 500.

In another embodiment of this low bandgap polymer, substituent W is —CF$_3$ and substituent Z is —SO$_2$R where R is —H or -alkyl. The n is again 5 to about 500.

Another low bandgap polymer of the present invention has the structure:

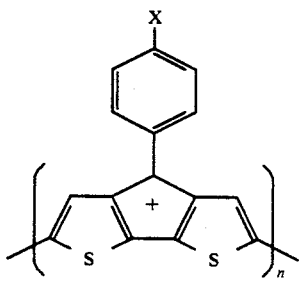

where X is —NO$_2$ —Cl, —OR$^1$ or —NR$^1$R$^2$ where R$^1$ and R$^2$ are independently H or alkyl. The n is again 5 to about 500.

BRIEF DESCRIPTION OF THE DRAWINGS

FIG. 3 shows structures of polyarene-methylidenes (III).

FIG. 4 shows structures predicted by others to have lowered E$_{gap}$'s (IV, V and VI).

i: 1)NaBH$_4$, 2)H$^+$ to produce VIIIa; ii: 1) RMgX, 2) TsCl, 3) LiAlH to give Z=R (XIIIa) or ii: 1) NaBH$_4$, 2) base then RX to yield Z=OR (XIIIb);

iii: CH$_2$(CN)$_2$, base (X); or W—CH$_2$—Z, base [where W $\neq$ Z = CN, COOR, CF$_3$, and the like];

iv: RCH$_2$NO$_2$, base on an imine derivative of IX v: 1) ArLi, 2) H$^+$, X=CH$_3$, Cl, H, OCH$_3$, or NR$_2$, for example.

Figure 12:
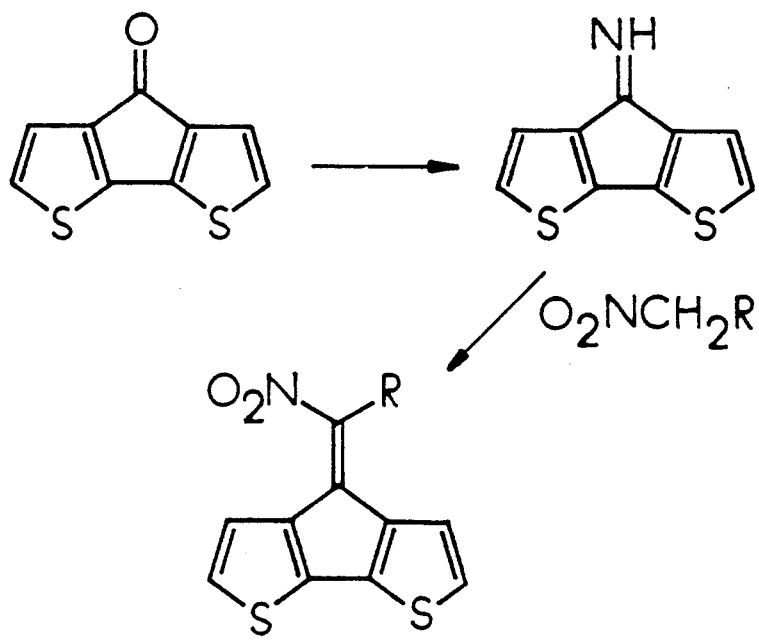

FIG. 12 schematically shows the synthesis of fused bithiophene monomers bearing NO$_2$ and an R group.

Figure 13:
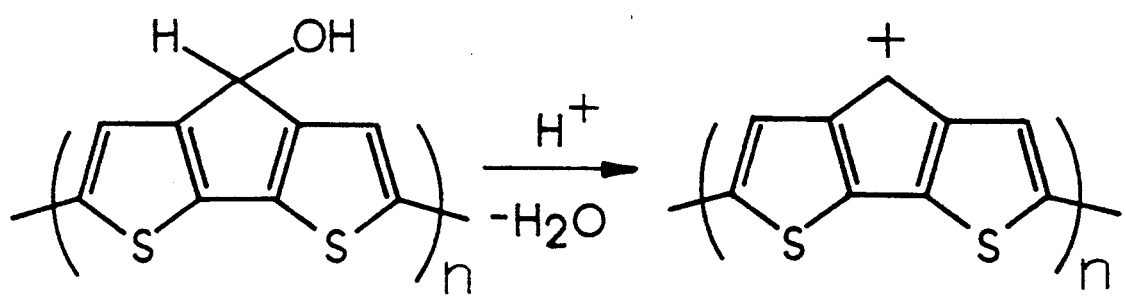

FIG. 13 schematically shows the production of polymeric VIIIa (where X is CH$^+$) from polymeric XIII where Z is OH.

Figure 14:
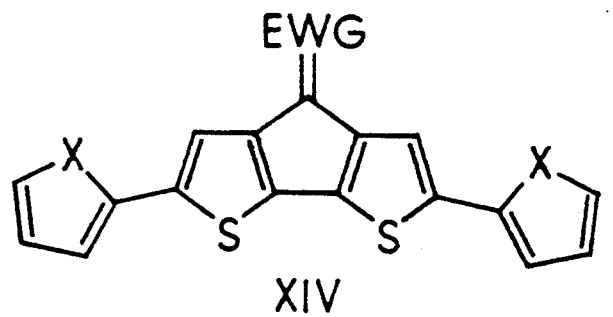

FIG. 14 shows a monomeric unit (XIV) for generating polymers with alternating monomer sequences (EWG = electron withdrawing group).

Figure 15:
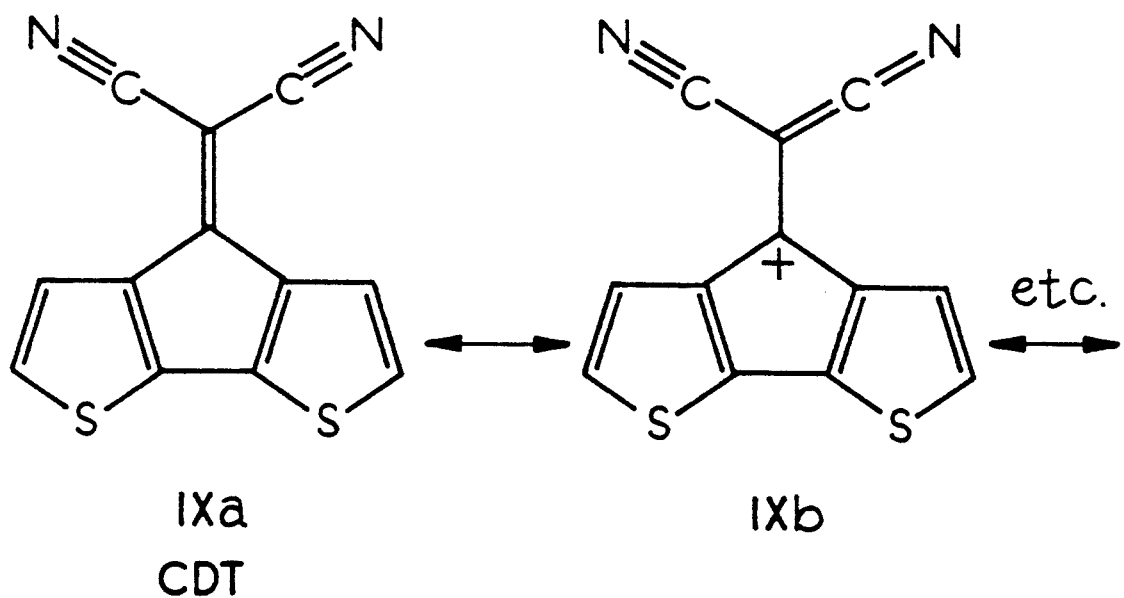

FIG. 15 schematically shows the monomeric structure of poly-4H-cyclopenta [1,2-b; 3,4-b']dithiophene-4-one (PCDT).

Figure 16:
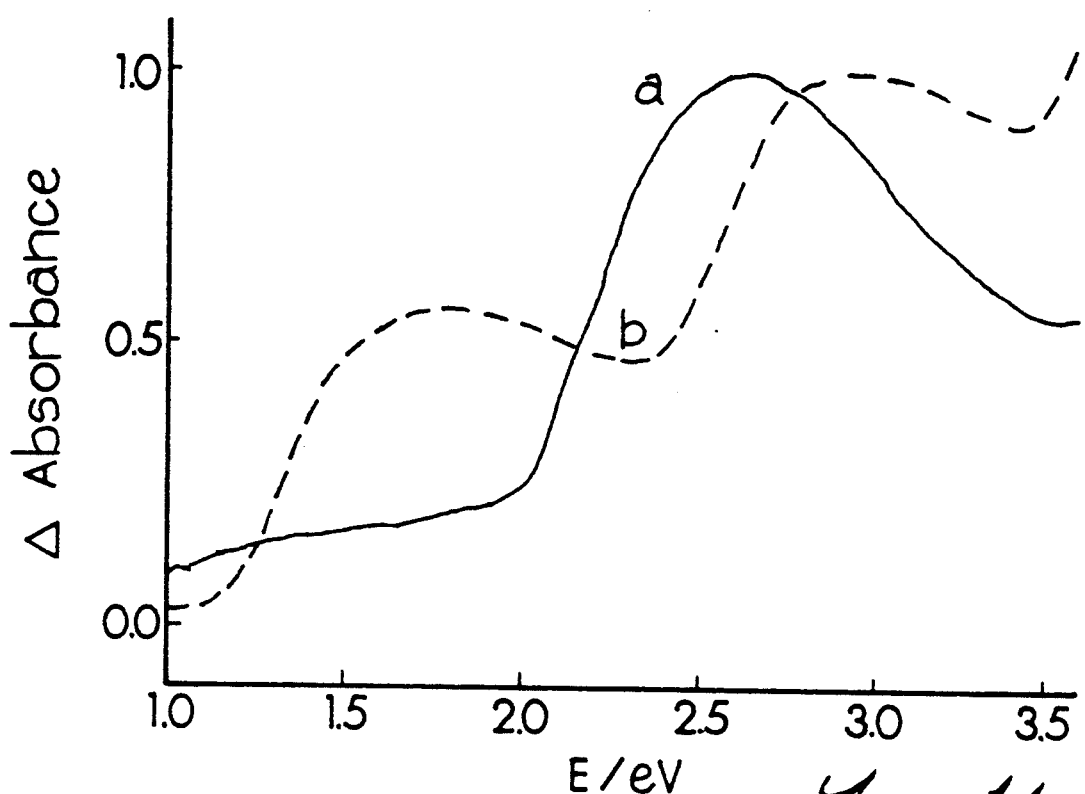

FIG. 16 shows the absorption spectrum for polythiophene (a) (solid line) and neutral poly-IX (b) (broken line).

Figure 17:
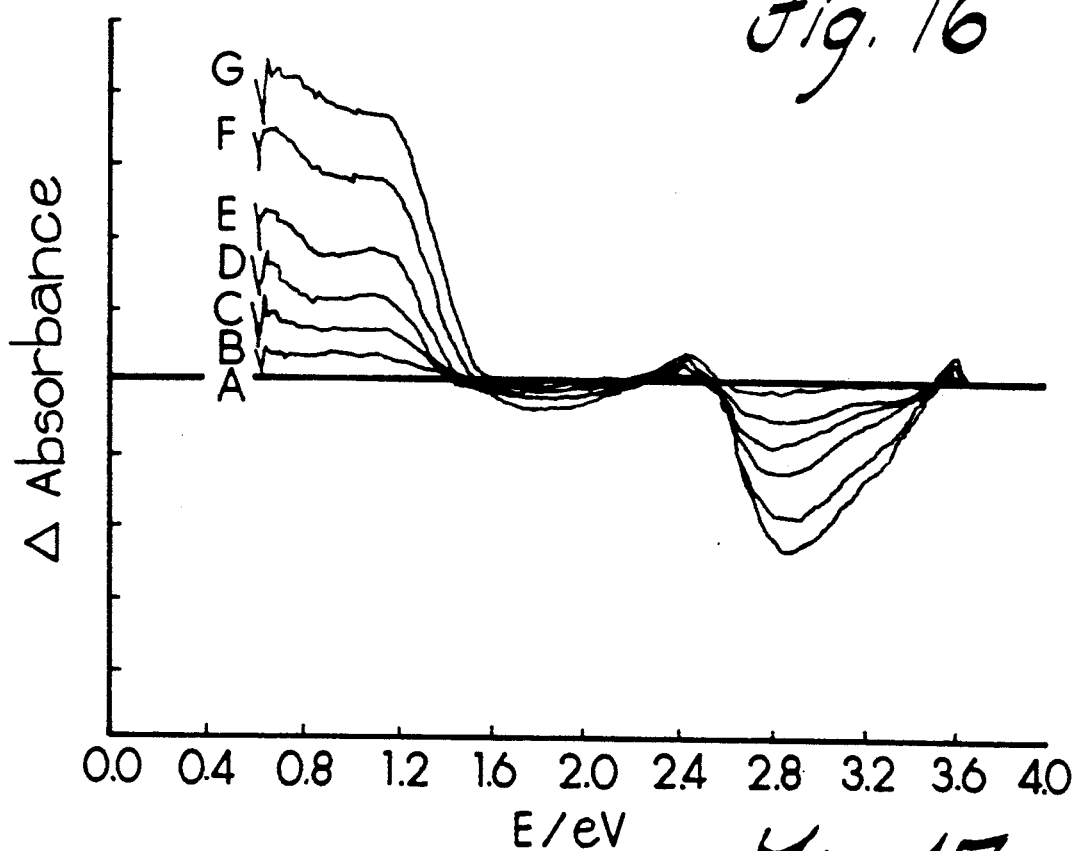
Figure 16:
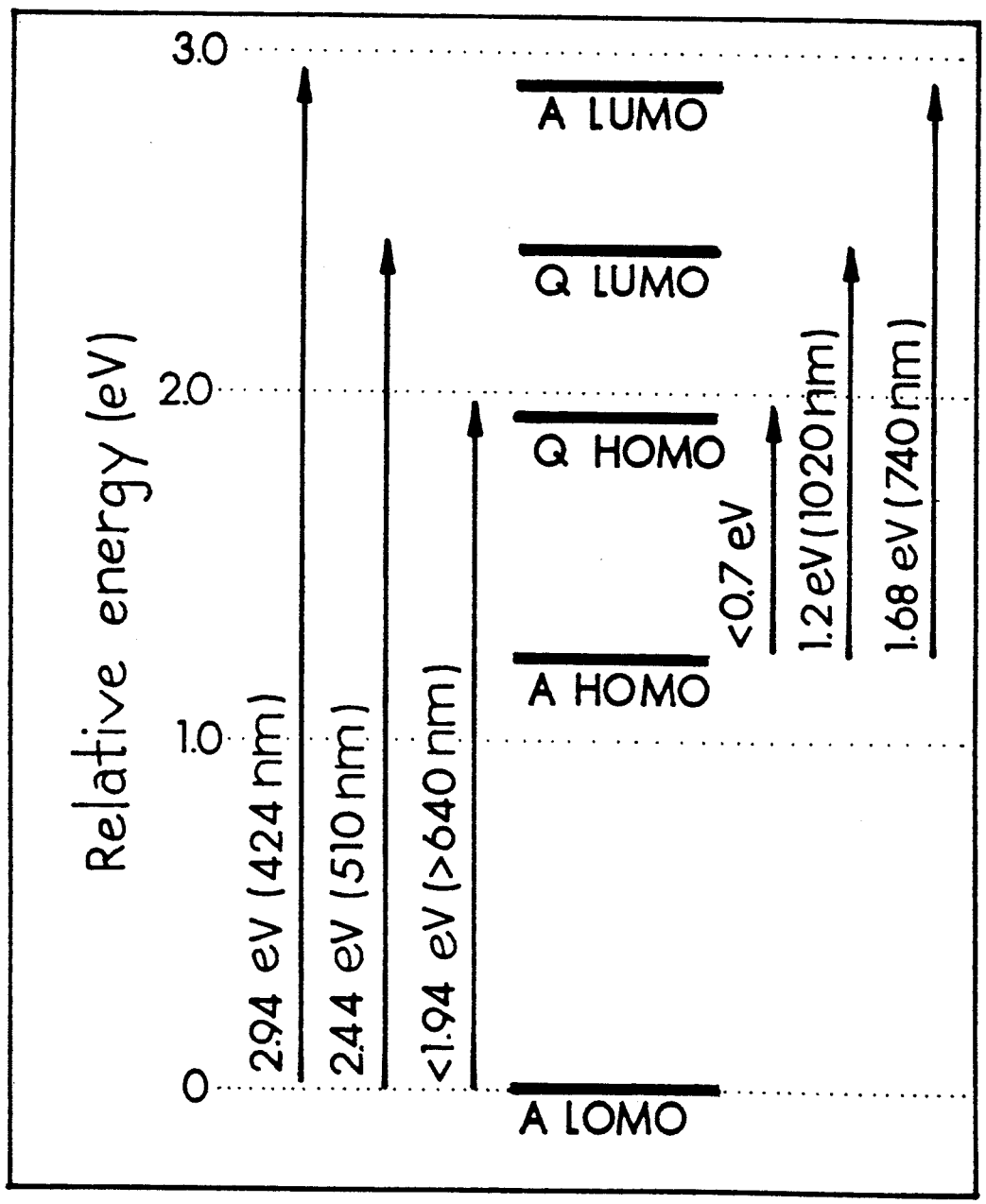

FIG. 17 shows the difference absorption spectra (reference to V$_{appl}$=2.5 V vs. Li) as a function of doping for poly-IX. A:2.8V, B:3.4 V, C:3.5V, D:3.6V, E:3.8V, F:3.9V, G:4.0V.

FIG. 18 shows approximate energy level diagram for poly-IX. Levels were estimated from spectral peak positions.

Figure 19:
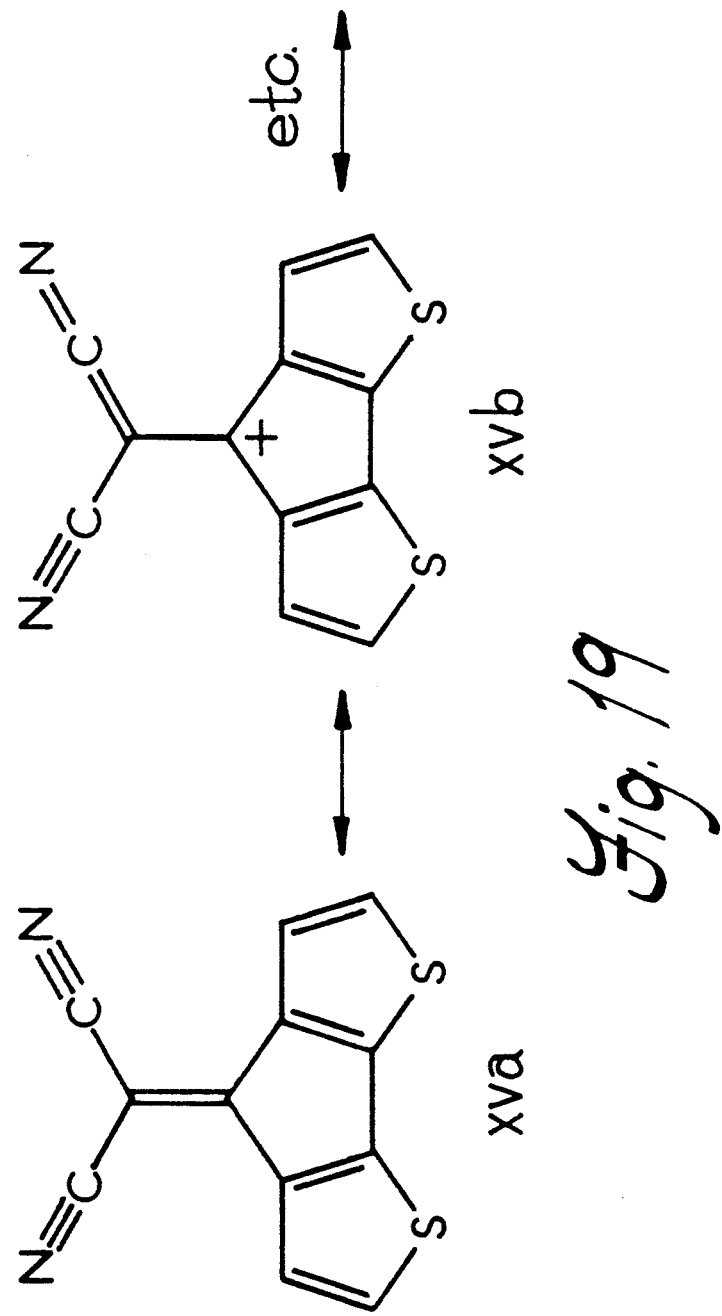

FIG. 19 schematically shows the monomeric structure of poly-4-dicyanomethylene-cyclopenta [2,1-b; 3,4-b']dithiophene-4 (PCDM) in two resonance forms (XVa and XVb).

Figure 20:
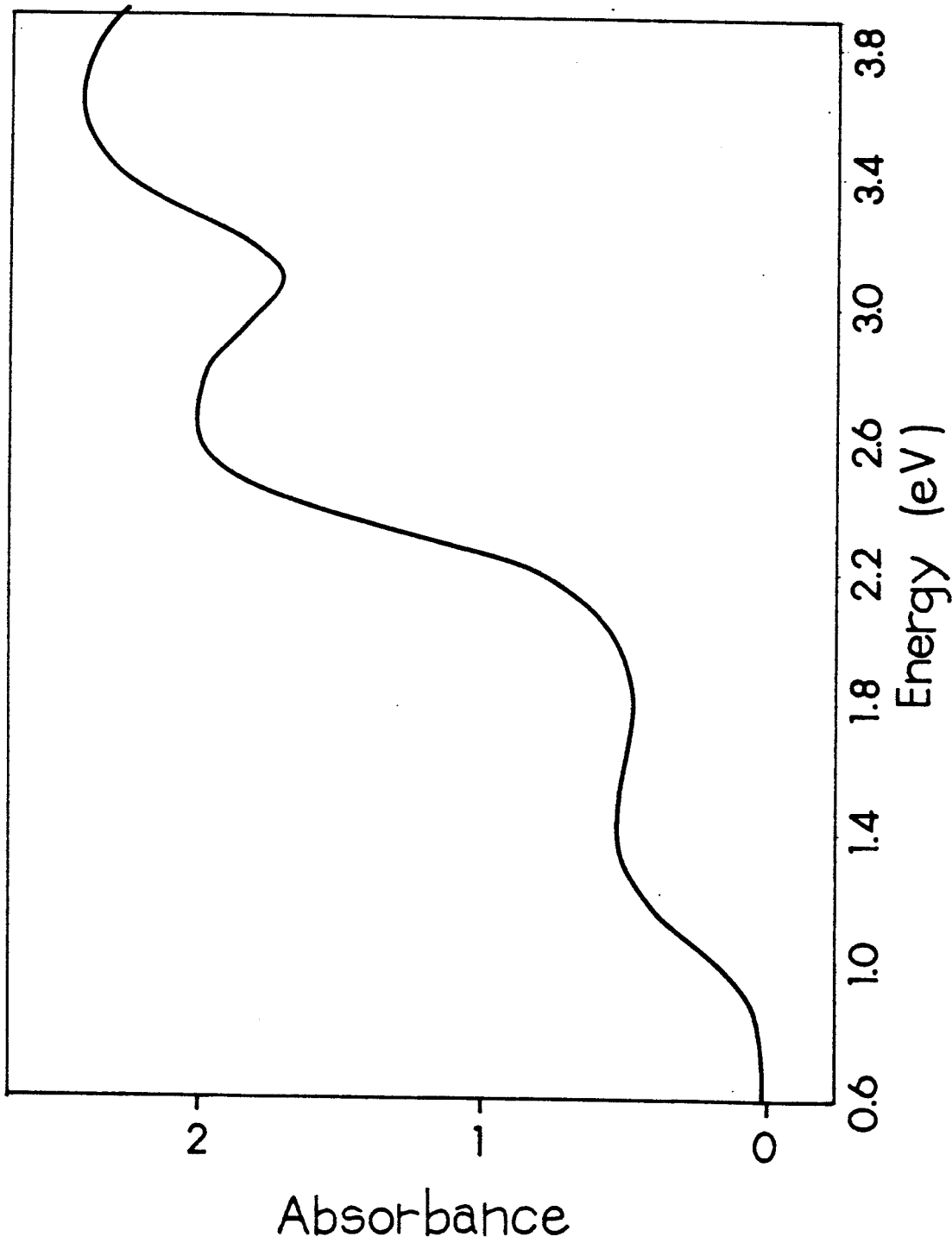

FIG. 20 shows the absorption spectrum for PCDM.

Figure 21:
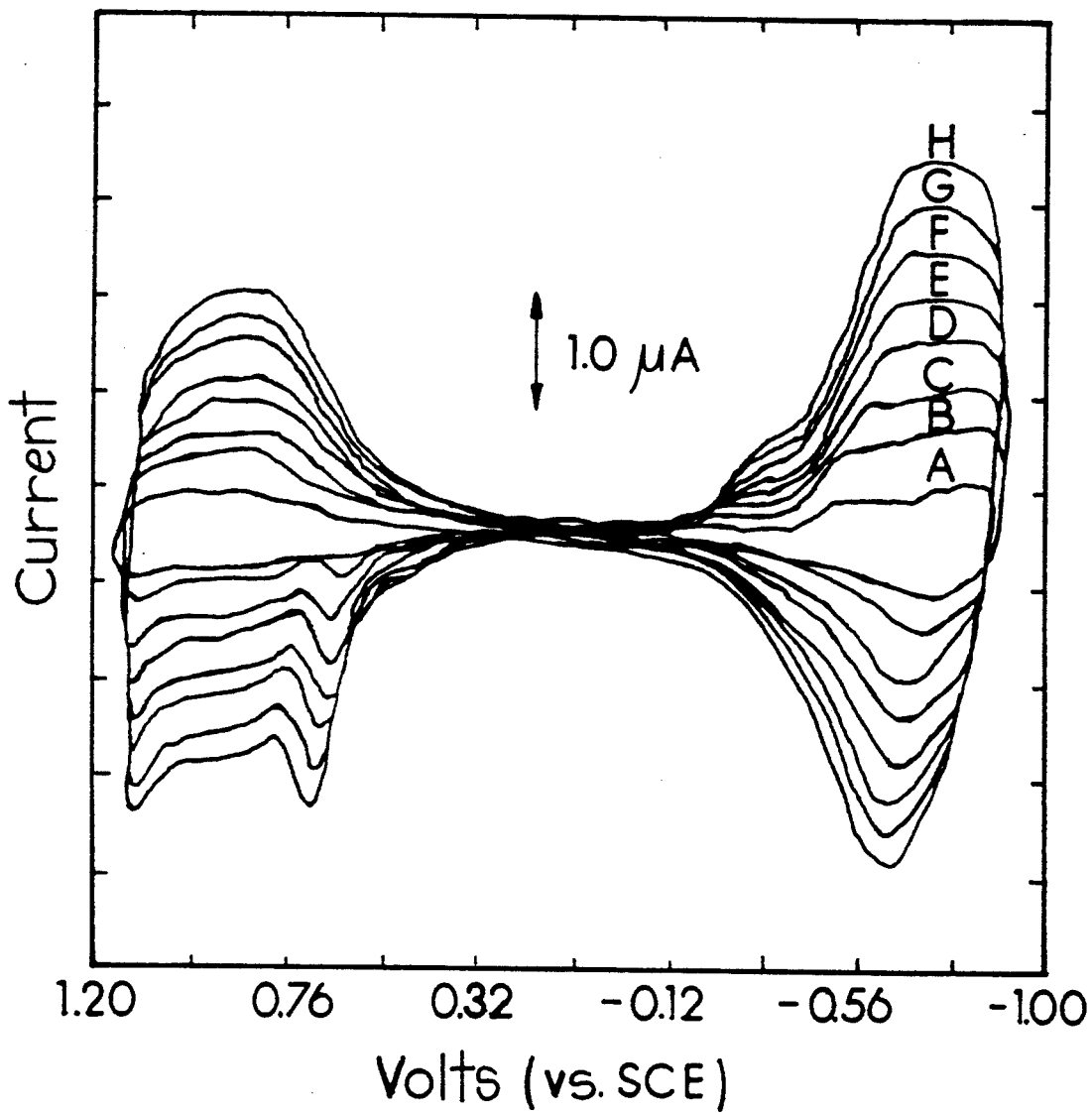

FIG. 21 shows a cyclic voltammogram of PCDM as a function of scan rate, showing p and n-doping. (a) 10 mV s$^{-1}$; (b) 20 mV s$^{-1}$; (c) 30 mV s$^{-1}$; (d) 40 mV s$^{-1}$; (e) 50 mV s$^{-1}$; (f) 60 mV s$^{-1}$; (g) 70 mV s$^{-1}$; (h) 80 mV s$^{-1}$.

Figure 22:
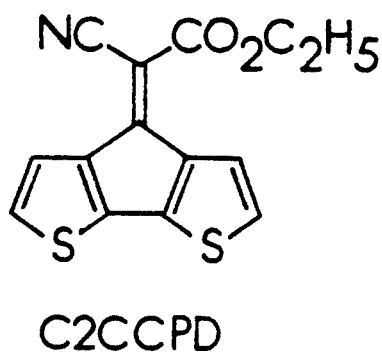

FIG. 22 shows the structure of carboxyethyl-cyanomethylene-4H-cyclopenta[2,1-b;3,4-b']dithiophene (C2CCPD)

Figure 23:
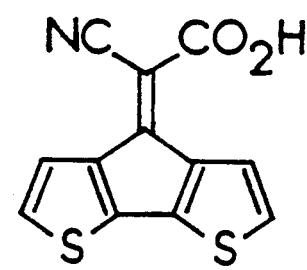

FIG. 23 shows the structure of carboxycyanomethylene-4H-cyclopenta[2,1-b;3,4-b']dithiophene (CCPD).

Figure 24:
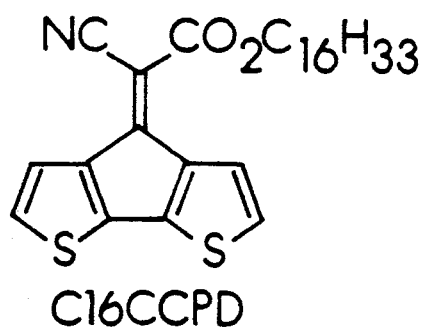

FIG. 24 shows the structure of carboxyhexadecyl-cyanomethylene-4H-cyclopenta[2,1-b;3,4b']dithiophene (C16CCPD).

Figure 25:
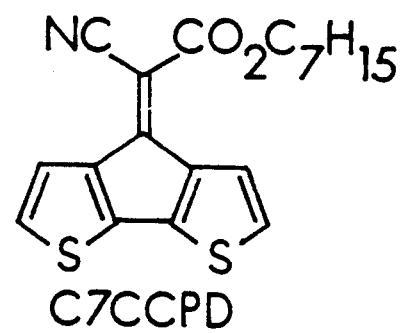

FIG. 25 shows the structure of carboxyhexyl-cyanomethylene-4H-cyclopenta[2,1-b;3,4-b']dithiophene (C7CCPD).

Figure 26:
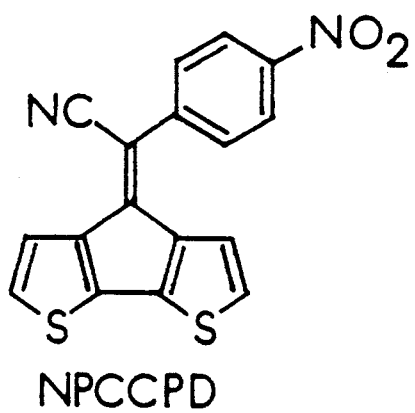

FIG. 26 shows the structure of p-nitrophenyl-cyanomethylene-4H-cyclopenta[2,1-b;3,4-b']dithiophene (NPCCPD).

Figure 27:
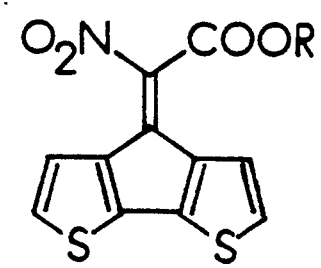

FIG. 27 shows the structure of compounds of the present invention, where W is NO$_2$, Z is COOR and R is H, alkyl or aryl.

Figure 28:
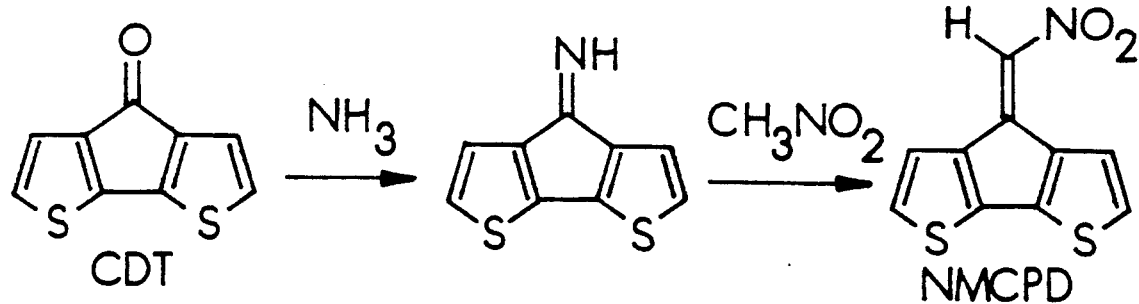

FIG. 28 schematically the synthesis of nitromethylene-4H-cyclopenta[2,1-b;3,4-b']dithiophene (NMCPD).

DESCRIPTION OF THE PREFERRED EMBODIMENTS

Figure 10:
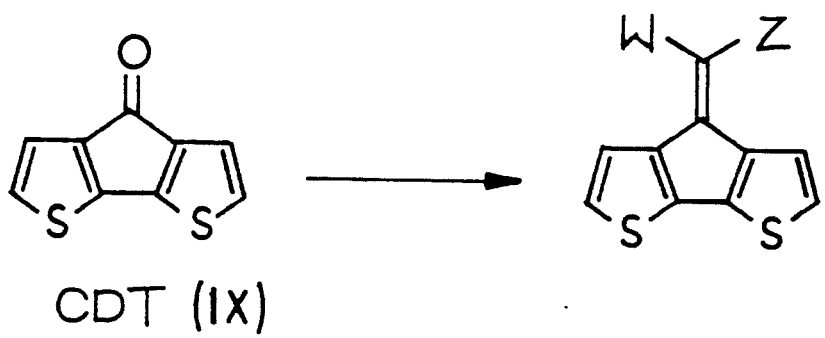
FIG. 10 shows the structure of cyclopenta[1,2-b;3,4-b']dithiophen-4-one (CDT) and its SYMBOLIC conversion to compounds of the present invention.

The monomer cyclopenta[1,2-b;3,4-b']dithiophene-4-one (CDT) (see FIG. 10) serves as a convenient starting point for other monomer systems. Reaction with active methylene compounds, WCH$_2$Z where W and Z come from a large list of groups including: —CN, —NO$_2$, esters, amides, sulfoxides, sulfones, sulfonates, sulfonamides, aldehydes, ketones, haloalkyls, alkyls, and the like, is straightforward. Examples are given below.

Figure 8:
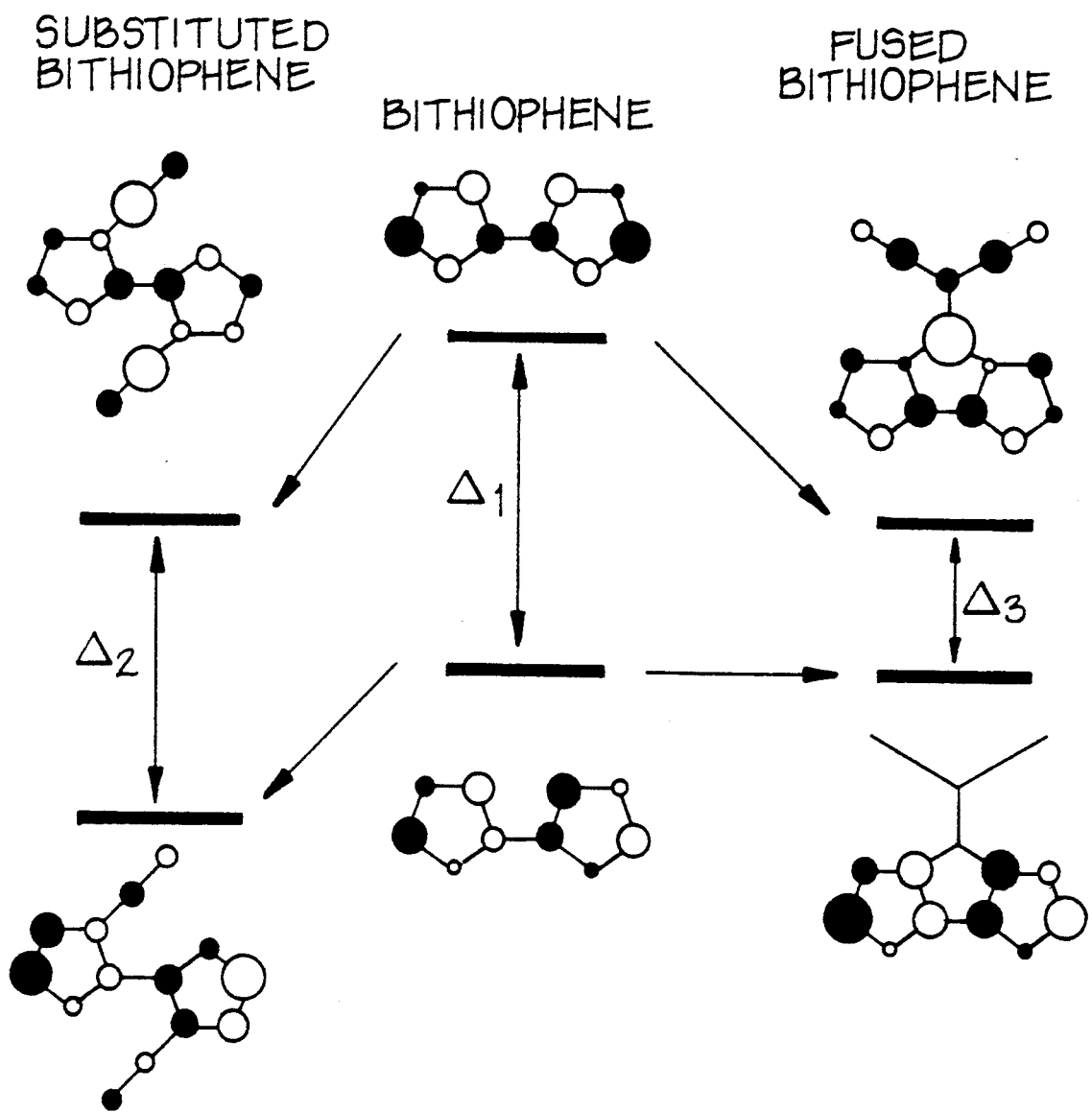
FIG. 8 shows frontier orbitals of bithiophene, a substituted bithiophene (3,3'-dicyanobithiophene), and a fused bithiophene (CDM). The HOMO-LUMO separations (and hence E$_{gap}$'s) follow the order $\Delta_1 > \Delta_2 > \Delta_3$.

The systems described herein are unusual in several respects. First the monomers CDT and CDM have essentially the same peak anodic potentials (E$_{pa}$'s) as α-bithiophene (BT). This behavior is quite different from other thiophene monomers substituted with electron withdrawing groups which have E$_{pa}$'s considerably higher (Waltman, et al., 1984) than the parent thiophene. Secondly, the E$_{pa}$'s of the corresponding polymers, PCDT, PCDM and PBT are approximately equal. Despite these similarities, the bandgaps are dramatically different. The obvious conclusion is that the energy of the HOMO level is not being strongly affected by substitution while the LUMO energy is being lowered. This can be explained with the aid of FIG. 8 which displays the frontier orbitals for bithiophene, a substituted bithiophene (3,3'-dicyanobithiophene) and fused bithiophene, CDM. The respective HOMO-LUMO energy separations are $\Delta_1$, $\Delta_2$ and $\Delta_3$.

Both the HOMO and LUMO of the substituted bithiophene are stabilized compared to bithiophene when electron withdrawing groups are placed at the 3 and 3' positions. (See the left side of the FIG. 8). The LUMO is stabilized to a slightly greater degree, leading to a small reduction in HOMO-LUMO separation ($\Delta_2 < \Delta_1$). The situation is dramatically different for the fused system, however. (See right side of FIG. 8). The antisymmetry of the HOMO in the fused system creates a node at the 4-position making this orbital relatively insensitive to substitution there. This is the origin of the similar $E_{pa}$s of BT, CDT and CDM and the analogous grouping of the $E_{pa}$s for their corresponding polymers. The symmetric LUMO for the fused system, however, is still stabilized by substitution with electron withdrawing groups (manifested by lowered half-wave reduction potentials). The $E_{178}$s for CDM, CDT and BT are $-0.78$ V, $-1.17$ V (Koster, et al., 1974) and $< -2.00$ V vs SCE (Jones et al. 1990), respectively. Since the reference HOMO level has not changed upon substitution, the net effect is a significantly reduced $E_{gap}$! ($\Delta_3 << \Delta_1$). Since $E_{gap}$'s have been shown to parallel the Huckel HOMO-LUMO separations (Kertesz, et al., 1989), this method can be used to rapidly screen monomers as to their potential of producing low $E_{gap}$ systems.

Figure 9:
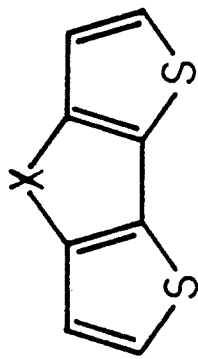
FIG. 9 shows a comparison of predicted and measured trends for (a) HOMO energies with peak anodic potentials, and (b) HOMO-LUMO separation with E$_{gap}$'s.

To a first approximation, the HOMOs and the peak anodic potentials of other fused bithiophene monomers should be approximately the same (the $E_{pa}$s of the corresponding polymers should also group at some lower value), regardless of the substituent. FIG. 9 gives the measured $E_{pa}$ for several monomers/polymers of the present invention, along with the calculated HOMO-LUMO differences and the associated bandgaps determined from their optical absorption spectra. These several cases support the generality of the model.

Figure 1:
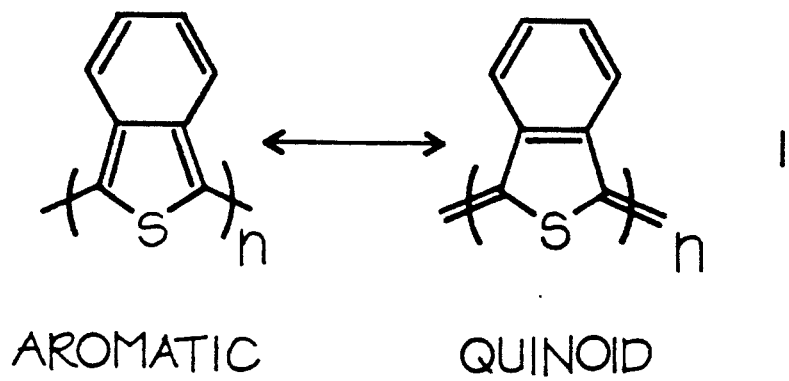
FIG. 1 shows the aromatic and quinoid character of polyisonapthalene polymers (I).
Figure 2:
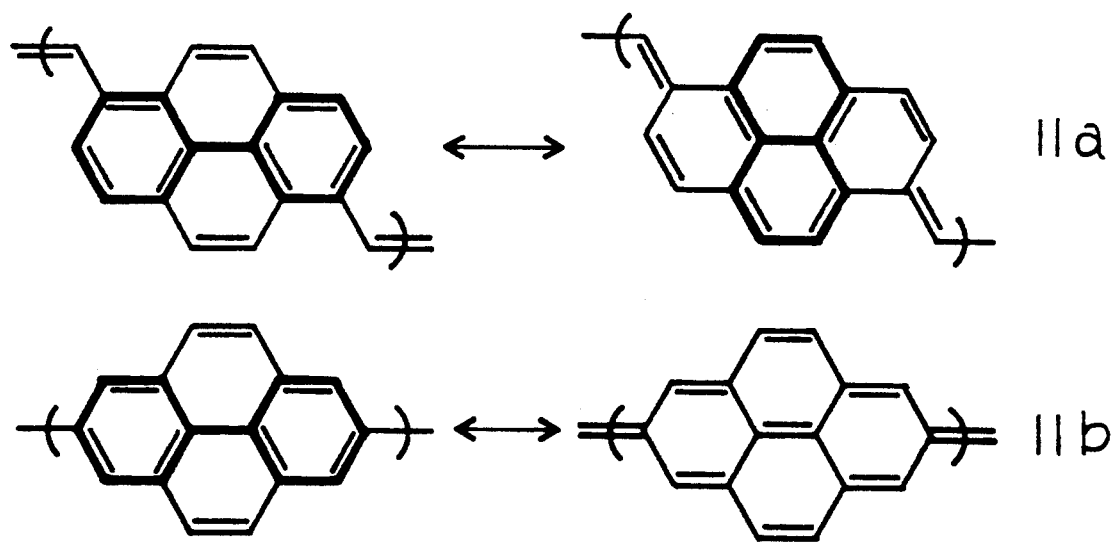
FIG. 2 shows the aromatic and quinoid character of poly (2/7-pyrenylene vinylene), (IIa and IIb).
Figure 5:
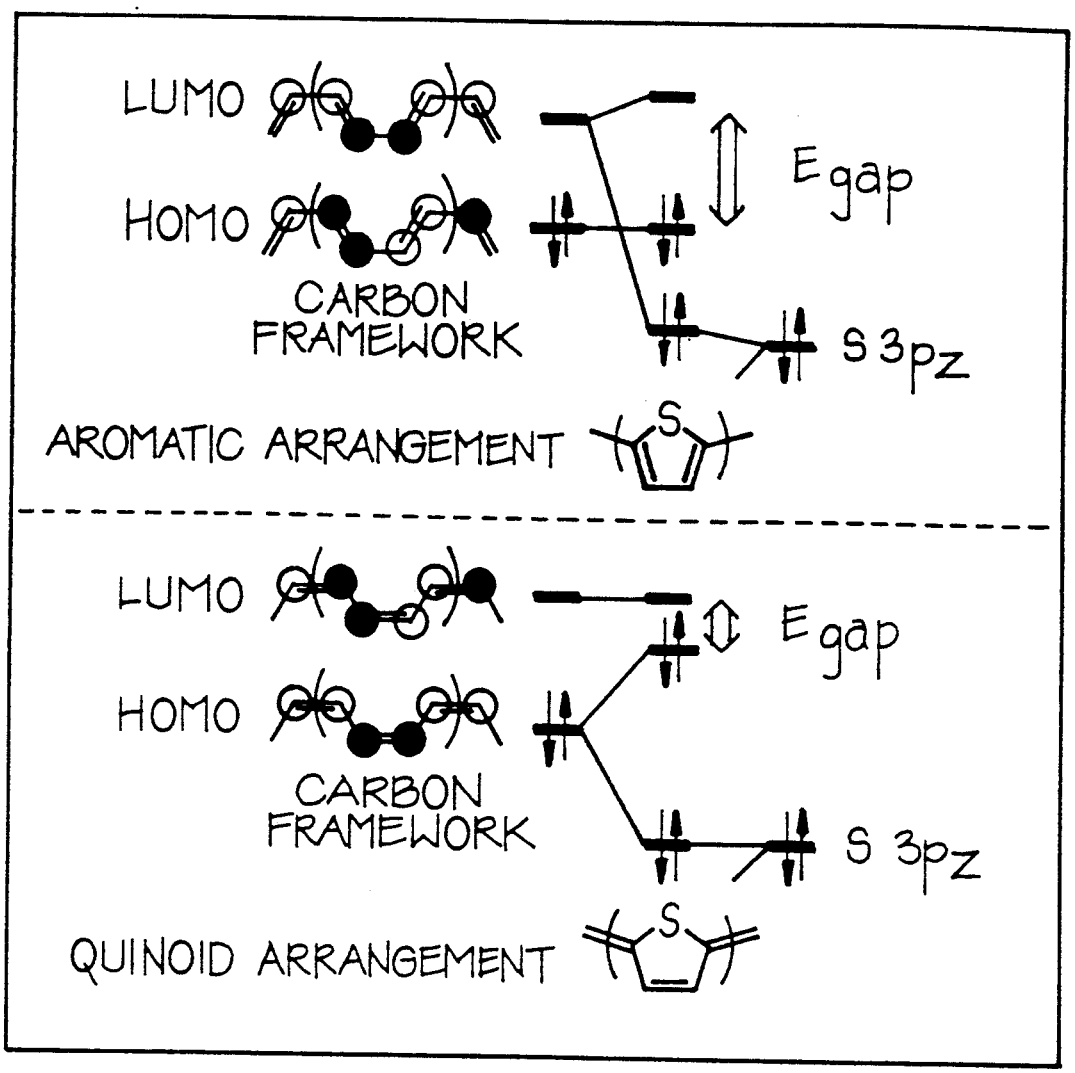
FIG. 5 shows E$_{gap}$'s for polymers with carbon frameworks in aromatic and quinoid arrangements.
Figure 6:
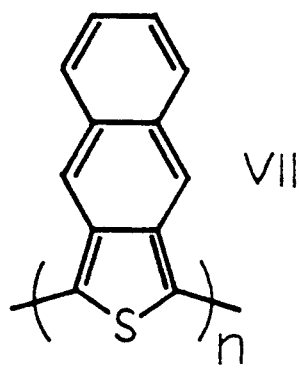
FIG. 6 shows the structure of a polymeric unit of PITN with a second annulated ring (VII).
Figure 7:
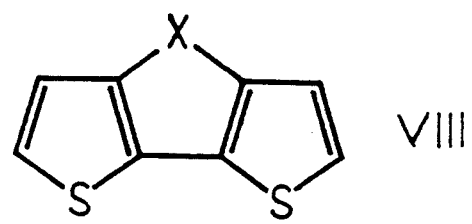
FIG. 7 shows the generalized fused bithiophene structure VIII.

FIG. 7 shows fused bithiophene structure VIII. The monomer/polymer families labelled IX, X and XI (see FIG. 11) are thus far most clearly understood. Compound VIII and family XII (see FIGS. 7 and 11) should also display small bandgaps but are yet incompletely defined. The acid-catalyzed dehydration step with VIII and XII to form the polycations has yet to be fully defined.

Monomer Family

Figure 11:
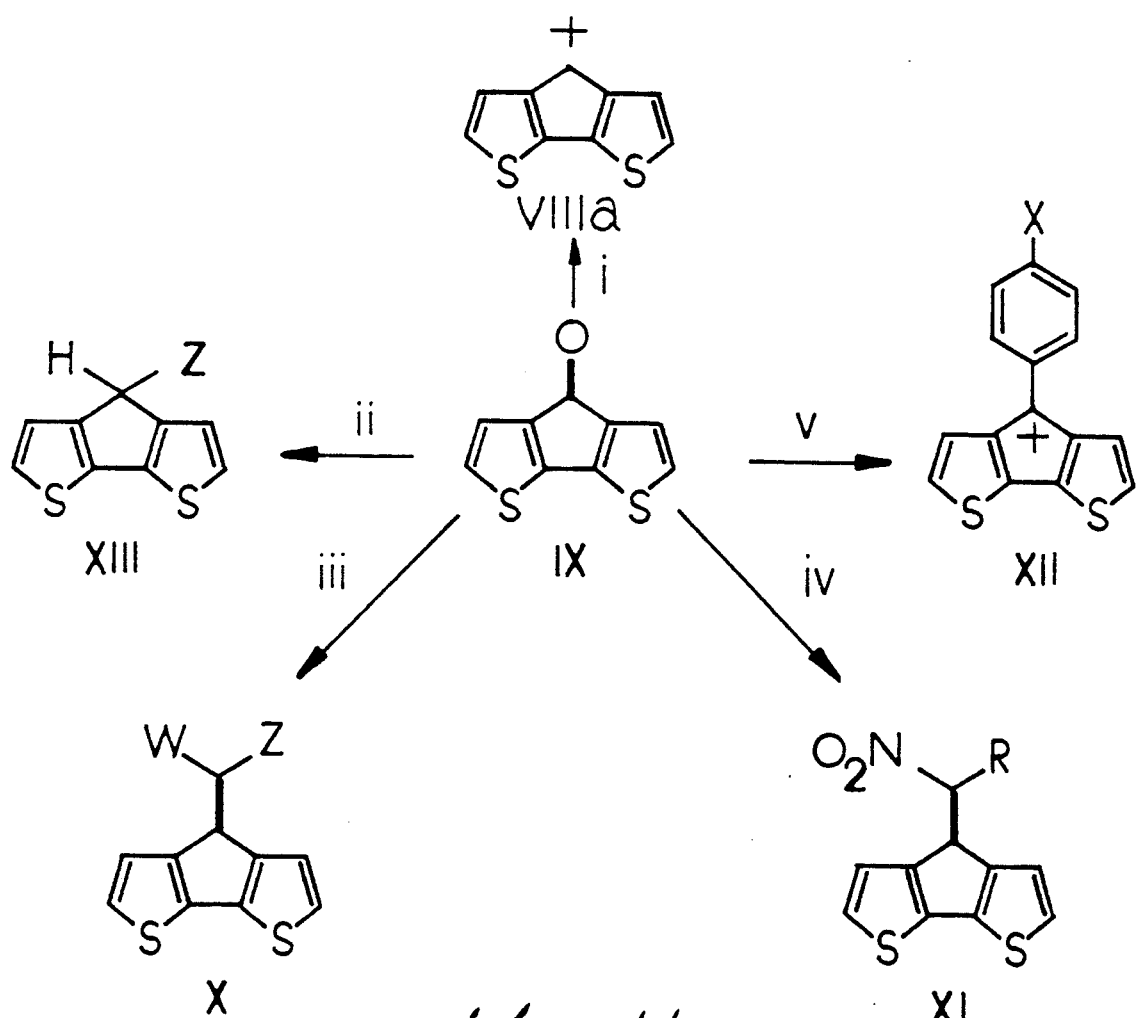
FIG. 11 shows synthetic schemes for certain monomers.

One member of family X, namely CDM where W =Z =CN (XV, see also FIG. 19) as shown in FIG. 11 is discussed in detail elsewhere herein. Its polymer has the lowest $E_{gap}$ known to date and displays reversible p-and n-type doping. Other family members (e.g., W =CN; Z =COOX) are prepared by the analogous Knoevenagel condensation chemistry of cyanoacetic acid derivatives with IX. Initial results are particularly good on the systems where X=H, $C_2H_5$, n-$C_7H_{15}$ and n-$C_{16}H_{33}$. Those skilled in the art understand that a variety of other alkyls will function likewise. These monomers all have $E_{pa}$s around 1.2 V (vs SCE) and their polymers display electronic absorption thresholds at $<0.9$ eV. The very moderate increase in $E_{gap}$ for these polymers compared to PCDM is consistent With the somewhat lowered electron withdrawing ability of a carboxyl compared to a nitrile (for various approaches and parameters quantifying substituent effects see "Mechanism and Theory in Organic Chemistry," Lowry, et al.). They are still below 1 eV, though, and there is now a convenient functionality (i.e., the X group of the ester) with which to alter mechanical/solubility properties. Since different n-alkyl substituents will not significantly affect the electronics of the ester, copolymers of various cyanoester derivatives can also be used to optimize the physical properties. Similarly, X can be ethylene oxide oligomers or ω-alkylsulfonates. Each imparts enhanced (aqueous) solubility and the latter leads to "self-compensating" (Havinga, et al., 1989; Patil, et al., 1987; Reynolds, et al. 1988) polymers. Since the $E_{gap}$'s will be below 1 eV, lowered doping levels will be required to obtain electrical conductivity.

Based on the strong electron-withdrawing abilities of the nitrile and nitro groups, the condensation products between IX and nitroacetonitrile (W=CN, Z=$NO_2$) or dinitromethane (W=Z =$NO_2$) afford polymers with $E_{gap}$'s even lower than PODM ($E_{gap} \leq 0.8$ eV). The dinitromethylene derivative of fluorenone is a known compound and is made through the action of iodonitroform with fluorene (Gabitov, et al., 1969).

The present invention involves a design strategy which appreciates that the quinoid structure arises at the expense of aromatic character but utilizes a different mode to reduce the latter. The monomers of the present invention are conceptually based on the antiaromatic ($12\pi$ electron) system, shown in FIG. 7, (VIIIa, X=$CH^+$) which displays a reduced HOMO-LUMO separation (Zhou, et al., 1989) compared to related aromatic (14 $\pi$ electron) fused systems (e.g., VIII; X =S (Jow, et al., 1986), O, or NH). Simple Huckel calculations give HOMO-LUMO differences of 0.162, 1.113, 1.038 and 1.116$\beta$ for the X=$CH^+$, S, O and NH derivatives of VIII, respectively. This model is successfully used to produce several low band gap polymers.

The monomers disclosed here possess a structure capitalizing on the antisymmetry of their highest occupied molecular orbitals (HOMO's) so as to have the energy of these states essentially uaffected by the incorporation of substituents at certain positions. The symmetry of the lowest unoccupied molecular orbitals (LUMO's) does allow for substituent effects on the energy of this orbital and is lowered when they are electron-withdrawing. This results in a reduction of the HOMO-LUMO separation and hence the bandgap ($E_{gap}$) This represents a new approach to reduced $E_{gap}$ polymers.

Polymers from these materials have likely use in electrochromics, electrode materials, semiconductor devices (diodes, thin film transistors, solar energy conversion, etc.). Electrochromic uses, for example, include: windows which darken or lighten upon application of a potential in autos, homes, commercial buildings; large scale flat displays.

The present invention also involves a new method for producing low bandgap ($E_{gap}$) polymers. The central feature involves using fused monomers with highest occupied ($\pi$) molecular orbitals (HOMOs) that are relatively insensitive to substitution and lowest unoccupied orbitals (LUMOs) whose energies depend strongly on these substituents. The polymer "bandgaps" parallel the HOMO-LUMO separations. The polymers of the present invention have the lowest $E_{gap}$'s reported to date and several new families are presented whose $E_{gap}$'s should be lower still. Strategies for increasing processibility while maintaining low $E_{gap}$'s are also provided. The environmental and mechanical difficulties that often plague doped polymers should be alleviated for our lowered bandgap materials. The apparent generality of certain fused thiophenes suggests several families of low bandgap materials. These are summarized in FIG. 11 Investigations have been conducted on representative members in a number of these. Compound IX is clearly an important starting material for these systems and can be obtained from a relatively straightforward literature procedure (Jordens, et al., 1970). In the following sections those systems on which the most proofs have been achieved are described.

FIG. 11 shows synthetic approaches to proposed monomers, i.1) $NaBH_4$, i.2)H ; ii.1) RMgX, ii.2) TsCl, ii.3) LAH to give Z =R (XIIIa) or ii.1) $NaBH_4$, ii 2) base then RX to yield Z=OR (XIIIb); iii) $CH_2(CN)_2$, base (X); or $W-CH_2-Z$, base [where $W \neq Z$=CN, COOR, $CF_3$, etc]; iv) $RCH_2NO_2$, base on imine derivative of IX (Charles, G., 1960) (the analogous reaction with the imine of fluorenone is known (Charles, G., 1963); v.1) ArLi, v.2) $H^+$, X =$CH_3$, Cl, H, $OCH_3$, $NR_2$, etc.

The large number of active methylene compounds that can undergo Knoevenagel-type reactions with IX allows extraordinary latitude in tailoring the properties of the resulting materials. Derivatives from readily available cyanoacetamides (W =CN, Z =$CONH_2$, CONHR, $CONR_1R_2$), ring-substituted phenylacetonitriles (W =CN, Z=—$C_6H_4$-X, X=—$NO_2$, halogens, —$NR_2$, —$NR^{30}{}_3$, —OR, -alkyl, for example), sulfones (e.g., W=—$CF_3$, Z=—$SO_2R$), nitroacetates (e.g., W=—$NO_2$, Z=—COOR) are but a few possibilities.

Active methylene compounds that can undergo condensations with carbonyl compounds may be used. Obviously, some would be better than others (especially the ones bearing strong electron withdrawing groups that remain in conjugation with the fused bithiophene system).

Monomer Family XI

The single nitro group in monomers based on XI is sufficient to lower the bandgap in their corresponding polymers to at least the level of PCDM. The processibility of this family of polymers is enhanced over PODM, due to the incorporation of alkyl substituents (R). These monomers are prepared according to Scheme I, shown in FIG. 12. This is the Henry reaction, an analogous condensation between nitroalkanes and fluorenone imine having been reported (Charles, 1963). This synthetic chemistry is used for preparing the derivative from nitroethane (R=$CH_3$). The higher homologs, e.g. R=$C_7H_{15}$ through $C_{16}H_{33}$ are also so prepared. This range of alkyl group length produces the best properties thus far noted for poly 3-alkylthiophenes with respect to processibility, effective degree of conjugation and ultimate conductivity (Roncali, et al., 1987).

Monomer Family XIII

One of the important criteria for good electrical conductivity in polymers is the ability of adjacent rings to assume substantially coplanar arrangements. Although the fused systems outlined in FIG. 11 have the advantage of forced coplanar arrangement of the thiophenes within the individual monomeric units, this does not guarantee that coplanarity can always be achieved between repeat units. It is known from studies on other substituted heteroaromatics that the introduction of substituents which increase the processibility of these polymers can sometimes present steric constraints to this coplanarity requirement (Ferraris, et al., 1989; Cannon, D.K. (1990); Ferraris, et al., 1990). Molecular mechanics calculations on several of the above mentioned oligomers show that the substituents are sufficiently far removed from the adjoining repeat unit so as not to interfere with the achievement of substantially coplanar arrangements. This is also the case for monomer family XIII. Even though the electronic factors are not expected to lead to materials with $E_{gap}$'s as low as families X and XI, polymers from family XIII benefit from the forced coplanarity in the repeat unit and possess significant processibility. The relatively straightforward chemistry leading to monomer family XIII facilitates a rapid optimization of the electrical-mechanical property balance.

Monomer VIIIa and Family XII

Monomer VIIIa shown in FIG. 7 where X is $CH^+$ is the simplest of these systems, but cannot be used to generate the corresponding polymer directly. Rather, the alcohol (XIII, Z =OH shown in FIG. 11) readily produced via reduction of CDT, can be polymerized into coherent films. Spectral measurements on acid-promoted doping of this polymer indicate that the amount of doping is controlled by the amount of acid which is introduced. Even though poly-VIII is a charged species, some stabilization is seen from the two flanking aryl rings (e.g., see FIG. 13).

Even higher stabilities of the polycation should be manifested by the poly-XII family since here the carbocation is flanked by three aromatic rings, at least two of which are held coplanar to the cationic orbital. Furthermore, substituents on the phenyl ring supply different amounts of electron density to this site, thus offering another method to control the electronics. The poly-XII family is generated from the corresponding alcohols and then subsequently dehydrated.

Copolymers

Since most of the monomers possess very similar $E_{pa}$'s, electrochemical copolymerization of them is feasible. This allows the best physical properties of processible polymers to be blended with low $E_{gap}$ polymers. Although the overall composition and/or sequence distribution of particular polymers will depend on the detailed kinetics of the propagation steps, such copolymerizations are less complicated than those between monomers of widely different oxidation potentials. Copolymers with alternating monomer sequences are generated from monomers like XIV (see FIG. 14). When the groups flanking the fused bithiophene moiety are comparatively electron rich, intramolecular redox leads to materials with even lower bandgaps (Kowalik, et al., 1991).

Described herein is a general method for obtaining families of low bandgap polymers and directions for development of this new class of materials. The polymers are characterized with respect to their electrical, electrochemical, optical properties and, where appropriate, mechanical properties. The environmental and mechanical problems that are often associated with doped polymers are greatly reduced in these systems.

The monomers of the present invention are readily polymerized, for example, to form polymers having from 5 to about 500 monomeric units. Such polymerization involves an initial dissolution of the monomers in a solvent which is stable to oxidative conditions, for example chloroform or nitrobenzene. Polymerization is typically initiated by electrochemical anodic effects or by chemical oxidants. Typical chemical oxidants which may be used include ferric chloride, ferric perchlorate, cupric perchlorate, and nitrosyl salts such as nitrosonium tetrafluoroborate ($NOBF_4$) and nitrosonium hexafluorophosphate (NOPF$_6$). Those skilled in the art may identify further oxidants likely to be usable. The polymerizations are carried out at ambient temperatures but elevated temperatures may also be used, if desired.

The following examples describe preferred embodiments and best modes of the present invention and are not intended to limit the scope of the present claimed invention unless otherwise so specified in the claims.

EXAMPLE 1

Narrow Band Gap Polymers: Polycyclopenta[1,2-b;3,4-b′9 dithiophen-4-one

An electroactive polymer with a lowered band gap is obtained from the monomer cyclopenta[2,1-b;3,4-b′]dithiophen-4-one, alternatively - Poly(4-oxo-4H-cyclopenta[2,1-b;3,4-b′]dithiophen2,6-diyl).

Much of the effort to date on narrow band gap heteroaromatic polymers focuses on increasing their quinoid character. The present design strategy recognizes that quinoid character arises at the expense of aromatic character and that other modes of reducing aromaticity are also effective in reducing $E_{gap}$. This approach is used to identify a family of monomers that yield lowered band gap materials compared to PT. Certain monomers of the present invention are based on the non-aromatic (12$\pi$ electrons) 4H-cyclopenta[2,1-b;3,4-b′]dithiophen-4-yl cation VII (X=CH$^+$) model which is expected to display a reduced HOMO-LUMO separation (Zhou et al., 1989) compared to related aromatic fused systems. Furthermore, incorporation of the empty p orbital at the 4-position affects the occupancy of the frontier orbitals similar to substitution by boron at that position which Tanaka et al. (Tanaka et al., 1985; Tanaka et al., 1987) have theoretically shown could reduce the band gap in other cases.

Since environmental stability of the cationic VIIa might be limited, (Koster et al., 1976) cyclopenta[2,1-b;3,4-b′]dithiophen-4-one IXa (FIG. 15) was chosen (Jordens et al., 1970) as a first approximation to it. Contribution from IXa's primary resonance form, IXb was expected to reduce the aromaticity of the system. The results of electrochemical and spectral studies on poly-IX are reported (Lambert et al., 1991).

Cyclic voltammetry: Repetitive cyclic voltammograms (RCV) of IX are obtained by multiple scans of a 0.01 mol dm$^{-3}$ solution of IX in nitrobenzene-tetrabutylammonium tetrafluoroborate (0.1 mol dm$^{-3}$) (TBATFB) between −0.63 and +1.47 (vs. SCE) at 100 mVs$^{-1}$. Cyclic voltammetry (CV) of poly-IX is accomplished by galvanostatically growing the polymer on the end of a 100 μm diameter platinum electrode, transferring the electrode to fresh electrolyte [nitrobenzene-TBATFB (0.1 mol dm$^{-3}$)], and scanning between 0.00 to +1.20 V (vs. SCE) at rates ranging from 5 to 100 mVs$^{-1}$. The peak anodio potential ($E_{pa}$) of the polymer is determined by extrapolation to zero scan rate. (SCE = Standard calomel electrode).

Spectroelectrochemistry: Thin films of poly-IX are deposited galvanostatically from 0.01 mol dm$^{-3}$ solutions of monomer in nitrobenzene-TBATFB (0.1 mol dm-3) onto indium/tin oxide (ITO) coated glass electrodes. Their spectroelectro-chemistry is examined in 0.1 mol dm$^{-3}$ LiBF$_4$-propylene carbonate (PC) by holding the film at a series of constant potentials and recording the spectra from 340 to 2100 nm.

The repetitive cyclic voltammetry (RCV) of IX is typical of a conducting polymer growing on the electrode with each scan. After several scans both monomer and polymer oxidation is observed, with the latter occurring at a lower potential. The $E_{pa}$ of IX is +1.26 V (vs. SCE) compared to +1.20 V (vs. SCE) for α,α′-bithiophene measured under identical conditions. Thus, to a first approximation, the carbonyl moiety does not appear to alter greatly the position of the HOMO in IX compared to α,α′-bithiophen. This is consistent with the antisymmetry of that orbital which places a node at the carbonyl. The $E_{pa}$ of poly-IX is +0.75 V (vs SCE) compared to +0.70 V (vs SCE) for poly (α,α′-bithiophene) (Skotheim, 1986) The peak anodic current is a linear function of scan rate, as expected for a substrate affixed to the electrode.

Ketone IX displays its lowest $\pi,\pi$ transition at $\lambda_{max}$=472 nm (Koster et al., 1979) ($\epsilon$=1250). The $\pi,\pi^*$ nature of this transition is supported by solvent effects and PPP ( Koster, 1979). Upon electropolymerization, this long wavelength absorption shifts to 740 nm in the neutral polymer [FIG. 16(b)], a red shift of ≧200 nm compared to PT [FIG. 16 (a)]. (Chung et al. 1984) A strong absorption at 425 nm is also present in poly-IX. The difference absorption spectra of this polymer as a function of applied potential (referenced to the neutral polymer, $V_{appl}$ =2.5V) are displayed in FIG. 17. The evolution of these spectra can be interpreted within the bipolaron formalism (Chung et al., 1984) if it is assumed that the lower energy absorption in neutral poly-IX is derived primarily from the aromatic HOMO-LUMO transition and the higher energy transition arises between some deeper level (ALOMO) and the LUMO. One then obtains the characteristic growth of the aromatic HOMO (AHOMO) to quinoid LUMO (QLUMO) and AHOMO to quinoid HOMO (QHOMO) bipolaron transitions (1.1-1.2 eV and ≦0.7 eV, respectively) as the polymer is p-doped to higher levels. Ordinarily this would be accompanied by a comparable decrease in the AHOMO-ALUMO absorption intensity. The observed apparent modest decrease in this absorption upon doping and the two isosbestic points at 2.5 and 2.3 eV can be rationalized with the approximate energy level diagram in FIG. 18. As the polymer is p-doped, the AHOMO→QHOMO, AHOMO→QLUMO, ALOMO→QHOMO and ALOMO→QLUMO transitions grow while AHOMO→ALUMO and ALOMO→ALUMO transitions decrease. The decrease in the AHOMO→ALUMO appears small because it is offset by increases in the ALOMO→QLUMO and ALOMO→QHOMO occurring over approximately the same wavelength range. The isosbestic points at 2.3 and 2.5 eV result from the overlap of the ALOMO→QLUMO and ALOMO→QHOMO transitions with the AHOMO→ALUMO transition. Similar arguments would be involved if the 424 nm transition were between the AHOMO and higher unoccupied aromatic and quinoid levels. The $E_{gap}$ of the neutral polymer, determined from the point of zero crossing of lightly doped polymer (Chung et al., 1984) (<3.4 vs. Li/Li+) is ≦1.2 eV. This gap is ≧ 08eV lower than that for PT (Chung et al., 1984) and only 0.2 eV higher than that of PITN. (Wudl et al., 1984).

This model, which proposes the incorporation of non-aromatic character as a route to reduce band gap polymers, succeeds for this polymer and it is noted that experiments on polymers derived from the Knoevenagel condensation product of IX with malononitrile and cyanoacetic esters also support this model. See following Examples) Poly-IX joins a select group of conducting heteroaromatic polymers with $E_{gap} < 1.5$ eV.

EXAMPLE 2

Narrow Bandgap Polymers: Poly-4H-cyclopenta[2,1-b; 3,4-b']dithiophene-4-dicyanomethylidene (PCDM)

An electroactive polymer with a bandgap of $\approx 0.8$ eV is obtained from the monomer 4-dicyanomethylene-4H-cyclopenta[2,1b;3,4-b']dithiophene, (ODM) (See FIG. 19).

The dicyanomethylene group in ODM (XV) shown in FIG. 19, is a stronger electron withdrawing substituent than the carbonyl in IX and should enhance the participation of XV's primary resonance contributor, XVb, to the overall structure of the molecule. This in turn is expected to reduce the HOMO-LUMO separation in the monomer, and the $E_{gap}$ in its polymer, PODM.

The UV/Vis spectrum of cDM displays a 100 nm (0.48 eV) red shift of the long wavelength absorption band compared to CDT ($\lambda^{IX}_{max} = 472$ nm, $\epsilon^{IX} = 1250$; $\lambda^{XV}_{max} = 576$ nm, $\epsilon^{XV} = 1450$). This band was assigned as a $\pi - \pi^*$ absorption for IX. The analogous absorption in XV is assigned to a $\pi - \pi^*$ transition based on the presence of structure in this band, its 20 nm red shift from hexane to methanol, and by analogy to IX. Upon polymerization this band shifts to 950 nm in neutral PCDM, a red shift of $\approx 0.9$ eV compared to the monomer and similar in magnitude and direction to that observed upon polymerization of CDT.

The UV/Vis/NIR spectrum of neutral PODM (see FIG. 20) shows the long wavelength band edge ($E_{gap}$) at $\approx 0.8$ eV, making it one of the lowest bandgap polymers reported to date. [PCDM is grown galvanostatically onto indium tin oxide (ITO) coated glass electrodes at 750 mA/cm$^2$ for 3 min. from 0.01M solutions of CDM in nitrobenzene containing 0.1M tetrabutylammonium tetrafluoroborate (TBATFB), and then electrochemically reduced at +2.8V vs Li/Li$^+$.]Cyclic voltammetry (CV) of PODM yields a peak anodic potential ($E_{pa}$) of +0.76 V vs SCE [PCDM was grown on a 100 μm dia Pt disk electrodes from 0.1M solutions of CDM in nitrobenzene containing 0.1M TBATFB and then rinsed with nitrobenzene. The $E_{pa}$ is determined by extrapolating to zero scan speed a series of CV's taken between 0.0 and +1.2 V vs. SCE.]For comparison, PODT and polybithiophene (PBT) display $E_{pa}$'s at +0.75 (Lambert et al. 1991) and +0.70 (Skotheim, 1986) V vs SCE, respectively. Anodic and cathodic CV (The potential was scanned from +0.16 to +1.16 to -0.89 to +0.16 V vs SCE) of PCDM (see FIG. 21) shows both oxidation and reduction of the polymer. (The source of the oxidation wave peaking $\approx 0.5$V vs SCE following each cathodic scan is not identified but it appears only if a cathodic scan precedes an anodic scan. This oxidation wave shows no discernible reduction. It appears associated with the adsorbed polymer rather than an impurity in solution since its current is linearly related to scan rate.) The difference in the threshold potentials for hole (p-doping) and electron (n-doping) injection is $\approx 0.3$V, comparable to that of PITN (Kobayashi et al., 1985; Kobayashi et al., 1987), and indicative of a narrow $E_{gap}$ material (Kaufman et al., 1983). However, whereas PITN is unstable to n-doping (Amer et al., 1989), PCDM appears stable to both p and n-doping after repeated anodic and cathodic cycling. FIG. 21 shows a cyclic voltammogram of PCDM as a function of scan rate, showing p and n-doping. (a) 10 mV s$^{-1}$; (b) 20 mV s$^{-1}$; (c) 30 mV s$^{-1}$; (d) 40 mV s$^{-1}$; (e) 50 mV s$^{-1}$; (f) 60 mV s$^{-1}$; (g) 70 mV s$^{-1}$; (h) 80 mV s$^{-1}$.

Dicyanomethylene-4H-oyolopenta[2,1-b;3,4-b']dithiophene (CDM)

In the above embodiment, malononitrile (0.26 mmole) in 10 mL of 95% ethanol is added to550 mg (0.26 mmole) CDT in 25 mL of 95% ethanol which contained 2 drops of piperidine. The reaction mixture is stirred at room temperature of 10 min., the residue filtered and washed with water. Recrystallization one time from acetonitrile gives analytically pure ODM (e.g. 56 mg, 93% yield), m.p. 257–258 C. Elemental Analysis: Found [Calculated]for $C_{12}H_4N_2S_2$:%C, 59.58 [59.98]; %H, 1.82 [1.68]; %N, 11.27 [11.66]. uv/vis: $\lambda_{max}$ (e):576nm (1450).

EXAMPLE 3

Cyanoester and Amide Derivatives

Cyanoester and amide derivatives are also prepared by analogous Knoevenagel-type condensation reactions involving cyanoacetic acid esters or amides (NCCH$_2$COX; X =OR where R is derived from an alkyl or aryl alcohol or X is NRR' where R and R' are various combinations of H, alkyl and aryl substituents). Typical procedures for several of these are as follows.

EXAMPLE 4

Carboxyethyl,cyanomethylene-4H-cyclopenta[1,2-b;3,4b']b']dithiophene (C2CCPD)

In another embodiment, ethylcyanoacetate (0 26 mmole) in 10 ml absolute ethanol is added to 50 mg (0.26 mmole) of cDT in absolute ethanol e g., 25 ml containing potassium hydroxide, e.g., 10 mg. A reflux condenser is fitted to a drying tube and the mixture refluxed for 12 hours, poured into 25 ml water and then extracted, e.g., 3X with dichloromethane e.g., 20ml. The organic layer is washed with 20 ml of aqueous NaHCO$_3$, dried, e.g., over anhydrous MgSO$_4$, filtered and the solvent removed in vacuo. The residue is recrystallized from 20 ml acetonitrile to afford analytically pure C2CCPD, see FIG. 22 (e.g., 45 mg, 60% yield), mp 164–65 C. Elemental Analysis: Found [Calculated]for $C_{14}H_9N_1O_2S_2$: %C, 58.18 [58.52]; %H, 3.35 [3.16]: %N, 4.63 [4.87].

EXAMPLE 5 carboxyoyanomethylene-4H-cyclopenta[2,1-b;3,4-b']dithiophene (CCPD)

CCPD (see FIG. 23) is prepared in 71% yield in a procedure analogous to that for C2CCPD except for the substitution of cyanoacetic acid for ethylcyanoacetate.

EXAMPLE 6

Carboxyhexadecyl,oyanomelhylene-4H-cyclopenta[2,1-b;3,4=b']dithiophene (C16CCPD)

Hexadecylcyanoacetate (e.g., 170 mg, 0.55 mmole), 100 mg (e.g. 52 mmole) of CDT and e.g. 50 μM piperidine in benzene e.g., 5 ml are refluxed together e.g., overnight. The reaction mixture is chromatographed over silica gel with hexane elution. The C16CCPD (purple fraction) is collected (e.g. 108.8 mg, 44% yield, mp 73 C). (See FIG. 24).

EXAMPLE 7

Carboxyhexyl,cyanomethylene-4H-cyclopenta[2,1-b;3,4=b']dithiophene (C7CCPD) (FIG. 25)

Heptyl cyanoacetate (123.7 mg, .67 mmole), ODT (100 mg) and 50 μl piperidine are placed in 10 ml benzene and refluxed overnight. Chromatography over silica gel with hexane elution affords C7CCPD (e.g. 90.3 mg (48%yield)), m.p. 57 C.

EXAMPLE 8

Other active methylene derivatives (WCH2Z) may also be condensed with CDT with base catalysis. For example, ring-substituted arylacetonitriles (W =CN, Z =—$C_5H_4$—X, X =$H_1$—$NO_2$, halogens, $NR_2$, —$NR_3^+$, —OR, alkyl, aryl, and the like) are prepared by the following procedure.

p-Nitrophenyl,cyanomethylene-4H TM cyclopenta[2,-b;3,4b']b']ditbiophene (NPCCPD)

p-Nitrophenylacetonitrile (86 mg, 53 mmole), 100 mg CDT and 100 μl piperidine are placed in 3 mL of benzene and refluxed overnight. The reaction mixture is extracted with ether, subsequently washed with 10% acetic acid, aqueous $NaHCO_3$ then water, dried and the solvent removed in vacuo to afford 105 mg NPCCPD (e.g., 86% yield) mp 223-5C. See FIG. 26.

Derivatives where W=$NO_2$ and Z=COOR (R=H, alkyl, aryl) are also readily prepared from nitroacetates (themselves easily obtained from esterification of the dianion of nitroacetic acid obtained from the reaction of nitromethane with KOH). See FIG. 27.

EXAMPLE 11

Nitromethylene-4h-cyclopenta[2,1-b;3,4-b']dithiophene (NMOPD)

Nitroalkyl (or aryl) derivatives (W— —$NO_2$, Z=H, alkyl, aryl) are prepared by the Henry reaction on the imine of CDT.

CDT (e.g. 50 mg) is dissolved in methanol, e.g., 15 mL the solution saturated with anhydrous ammonia gas and the reaction vessel sealed. The mixture is allowed to stand at room temperature for one to two weeks after which it is neutralized (with, e.g., concentrate $H_2SO_4$) and the blue precipitate filtered. The collected solid is redissolved in concentrated aqueous ammonia and extracted with ether. The solution is dried over $MgSO_4$ and the solvent removed in vacuo. The remaining solid is dissolved in nitromethane, refluxed (e.g. overnight) and the reaction mixture evaporated to dryness. The product, NMCPD, is purified for example, by column chromatography over silica gel with $CHCl_3$ elution; m.p. 162-4 C. See FIG. 28.

Substitution of other nitroalkanes for nitromethane affords derivatives in which the —H has been replaced by alkanes or aryls.

Citations in the following list are incorporated by reference herein for the reasons cited.

CITATIONS

Amer, A., Burkhardt, A., Nkansah, A., Shabana, R., Galal, A., Mark, H.B. Jr., and Zimmer, H., (1989), *Phosphorous Sulfur and Silicon*, 42, 63.

Bakhashi, A.K., and Ladik, J. (1988), *Solid State Comm.*, 65:1203.

Bolognes, A., Catellani, M., Desti, S., Zamboni, R., and Taliani, R. (1988), *J.C.S. Chem. Comm.*, 245.

Bredas, J.L. (1985) *J. Chem. Phys.*, 82:3808.

Bredas, J.L. (1987), *Synthetic Metals*, 17:115.

Bredas, J.L., Heeger, A.J. and Wudl, F. (1986), *J. Chem. Phys.*, 85:4673

Bredas, J.L., Chance, R.R. and Silbey, R. (1982), *Phys. Rev.*, B26:5843.

Bredas, J.L., Themans, B., Andre, J.M., Chance, R.R. and Silbey, R. (1984), *Synthetic Metals*, 9:265.

Cannon, D.K., *Dissertation* (1990), The University of Texas at Dallas.

Charles, G. (1960), *Bull. Soc. Chim. Fr.*, 421.

Charles, G. (1963), *Bull. Soc. Chim. Fr.*, 1573.

Chung, T.C., Kaufman, J., Heeger, A.J. and Wudl, F. (1984), *Phys. Rev. B*, 30:702.

Colaneri, N., Kobayashi, M., Heeger, A.J. and Wudl, F. (1985), *J. Chem. Phys.*, 12:5717.

Colaneri, N., Kobayashi, M., Heeger, A.J. and Wudl, F. ((1986), *Synthetic Metals*, 14:45.

Ferraris, J.P., Andrus, R.G., Wiser-Halladay, R. and Hrncir, D.C. (1990), *New Polym. Mater.*, 2:41.

Ferraris, J.P., Andrus, R.G. and Hrncir, D.C. (1989), *J.C.S. Chem. Comm.*, 1318.

Gabitov, F.A., Fridman, A.L. and Niloaeva, A.D. (b 1969), *Zh. Org. Khim.*, 5:2245.

Grant, P.M. and Batra, I.P. (1979), *Solid State Commun.*, 29:225.

Hanack, M., Heiber, G., Dewald, G., Ritter, H., and Rohrig, U. (1991), *Polym. Mater. Sci. Engn.*, 64:330.

Havinga, E., ten Hoeve, W., Meijer, E. and Wynberg, H. (1989), *Chem. Mater.*, 1:650.

Ikenoue, Y., Wudi, F. and Heeger, A.J. (1989), *Synthetic Metals*, 40:1.

Ikenoue, Y. (1990), *Synthetic Metals*, 35:263.

Jenekhe, S.A. (1986), *Nature*, 322:345.

Jones, D., Guerra, M., Favaretto, L., Modelli, A., Fabrizio, M. and Distefano, G., *J. Phys. chem*, (1990) 94:5761.

Jordens, P., Rawson, G. and Wynberg, H. (1970), *J. Chem. Soc. (C)*, 273.

Jow, T.R., Jen, K.Y., Elsenbaumer, R.L., Shacklette, L.W., Angelopoulos, M. and Cava, M.P. (1986), *Synthetic Metals*, 14:53.

Kaufman, H., Chung, T.C., and Heeger, A.J. (1983), *Solid State Comm.*, 47:585.

Kertesz, M., Koller, J. and Azman, A., in *Photon, Electron and Ion Probes of Polymer Structure and Properties*, Dwight, D.W., Fabish, T.J. and Thomas, H.R., Eds., American Chemical Society: New York (1981), pg. 105.

Kertesz, M. and Lee, Y. (1989), *Synthetic Metals*, 28:C545.

Kertesz, M. and Lee, Y.S. (1987), *J. Chem. Phys.*, 91:2690.

Kobayashi, M., Colaneri, N., Boysel, M., Wudl, F. and Heeger, A.J. (1985), *J. Chem. Phys.*, 12:5717.

Kobayashi, M., Colaneri, N., Boysel, M., Wudl, F. and Heeger, A.J., European Patent Application No 87311095.1 (1987)

Kobmehl, G. (1983), *Makromolec. Chem. Rapid Commun.*, 639.

Koster, P.B., Janssen, M.J. and Lucken, E.A.C. (1974), *J.C.S. Perkin II*, 803.

Koster, P.B. and Janssen, M.J. (1976), *J. Chem. Soc., Perkin Trans.* 2, 323.

Koster, P.B. and Janssen, M.J. (1979), *J. Chem. Soc., Perkin Trans.* 2, 393 and references therein.

Kowalik, J. and Tolbert, L.M. (1991), *Poly. Mater. Engn. Sci.*, 64:214.

Lambert, T.L. and Ferraris, J.P., *J.C.S. Chem. Comm.* (1991) 752.

Lee, Y., Kertesz, M. and Elsenbaumer, R.L. (1990), *Chem. Mater.*, 2:526.

Lee, Y. and Kertesz, M. (1988), *J. Chem. Phys.*, 88:2609.

Longuet-Higgins, H.C. and Salem, L. (1959), *Proc. R. Soc. London Ser A.*, 251:172.

Lowe, J.P. and Kafafi, S.A. (1984), *J. Amer. Chem. Soc.*, 106:5837.

Lowry, T.H. and Richardson, K.S., "Mechanism and Theory in Organic Chemistry," (3rd Edition) Harper and Row, Publishers (New York), p. 143 ff.

Mintmire, J.W., White, C.T. and Elert, M.L. (1987), *Synthetic Metals*, 16:235.

Miyaura, N., Suzuki, A. and Yanagi, T. (1981), *Synth Commun.*, 11:513.

Otto, P. and Ladik, J. (1990), *Synth. Met.*, 36:327.

Paldus, J. and Chin. E. (1983), *Int. J. Quantum Chem.*, 24:373.

Patil, A.O., Ikenoue, YU., Basescu, N., Colaneri, N., Chen. J., Wudl, F. and Heeger, A.J. (1987), *synth. Met.*, 20:151.

Reynolds, J., Sundarensen, N.S., Pomerantz, M., Basak, S. and Baker, S.K. (1988), *J. Electroanal. Chem.*, 250:355.

Roncali, J., Garreau, R., yassar, A., Marque, F., Garnier, F. and LeMaire, M. (1987), *J. Phys. Chem.*, 91:6706.

Skotheim, T. A. (1986), *handbook of Conducting Polymers*, Marcel Dekker, Inc. New York, p. 302.

Streitweiser, A., (1961) "Molecular Orbital Theory for Organic Chemists", John Wiley and Sons, Inc., New York.

Taliani, C., Ruani, G. Zamboni, R., Bolognesi, A., Catellani, M., Desti, S., Porzio, W., and Ostoja, P. (1989) *Synthetic Metals*, 28, C507.

Tanaka, K., Murashima, M. and Yamabe, T. (1988), *T. Synthetic Metals*, 24:371.

Tanaka, K. Wang, S. and Yamabe, T. (1989), *Synthetic Metals*, 30:57.

Tanaka, K. Ueda, K. Koihe, T., Ando, M. and Yamabe, T. (1985), *Phys. Rev. B.*, 32:4279.

Tanaka, K. Yamanaka, S. Ueda, K., Shinji, T. and Yamabe, T. (1987) *Synthetic Metals*, 20:333.

Toussaint, J.M., Wudl, F. and Bredas, J.L. (1989)-1, *J. Chem. Phys.*, 91:1783.

Toussaint, J.M., Themans, B., Andre, J.M. and Bredas, J.L. (1989-2), *Synthetic Metals*, 28:205.

Waltman, R.J., Diaz, A.F. and Bargon, J. (1984), *J. Electrochem.*, 131:740,1452.

Wudl, F. Kobayashi, M. and Heeger, A.J. (1984), *J. Org. Chem.*, 49:3382.

Wudl, F., Ikenoue, Y. and Patil, A.O. (1990), *Nonlinear Optical and Electroactive Polymers*, Ulrich, D., Pradad, P.N., eds.; Plenum Press: New York, 1988, pg. 393.

Wudl, F. and Patil, A.O. (1988), *Macromol.*, 21:540.

Yamamoto, T., Sanechika, K. and Yamamoto, A. (1981), *Chem. Lett.*, 1079.

Zhou, Z. and Parr, R.G. (1989), *J. Amer. Chem. Soc.*, 111:7371.

Zimmer, H.A., Mulligan, K.J., Mark, H.B., Pons, S. and MacAleer, J.F. (1984), *J. Polym. Sci. Polym. Lett. Ed.*, 22:77.

Of course other substituents, particularly those known in the art to have electron-withdrawing effects may be substituted for those specified in many of the following claims. Such substituents for W and/or Z are viewed as equivalents.

What is claimed is:

1. A polymer having a bandgap of less than about 1 eV and the structure:

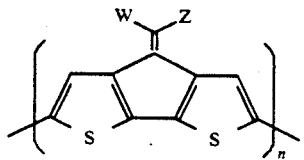

where
W is $-CF_3$ and Z is $-SO_2R$ where R is $-H$ or -alkyl; and
n is a number of monomeric units.

2. A polymer having a bandgap of less than about 1 eV and the structure:

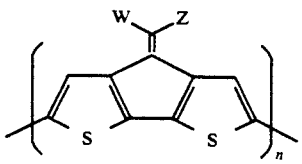

where
W is $-NO_2$ and Z is $CO_2R$ where R is $-H$ or -alkyl; and
n is a number of monomeric units.

3. A polymer having a bandgap of less than about 1 eV and the structure:

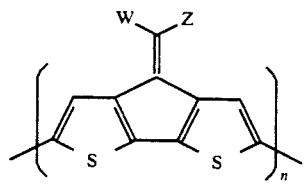

where
W and Z are $-CN$; and
n is a number of monomeric units.

4. A polymer having a bandgap of less than about 1 eV and the structure:

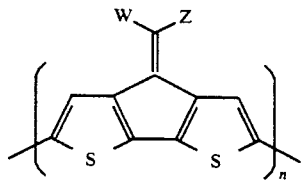

where
W is CN or $NO_2$ and Z is $CO_2R$ where R is H or $C_mH_{2m+1}$ and m is 1 to about 16; and
n is a number of monomeric units.

5. A polymer having a bandgap of less than about 1 eV and the structure:

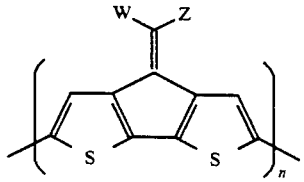

where
W is CN or $NO_2$ and Z is $C_6H_4NO_2$; and
n is 5 to about 500.

* * * * *